(12) United States Patent
Wen et al.

(10) Patent No.: US 7,939,184 B2
(45) Date of Patent: May 10, 2011

(54) AMINE COMPOUNDS, THEIR PREPARATION PROCESSES AND THE ORGANIC ELECTROLUMINESCENT DEVICES USING THE SAME

(75) Inventors: Shih-Wen Wen, Kaohsiung (TW); Yao-Shan Wu, Kaohsiung (TW); Huang-Ming Kau, Bade (TW)

(73) Assignee: E-Ray Optoelectronics Technology Co., Ltd., Taipei (TW)

( * ) Notice: Subject to any disclaimer, the term of this patent is extended or adjusted under 35 U.S.C. 154(b) by 897 days.

(21) Appl. No.: 11/819,576

(22) Filed: Jun. 28, 2007

(65) Prior Publication Data

US 2008/0038587 A1 Feb. 14, 2008

(30) Foreign Application Priority Data

Aug. 10, 2006 (TW) ................ 95129292 A

(51) Int. Cl.
*C07C 211/61* (2006.01)
(52) U.S. Cl. .............. 428/690; 313/504; 564/427
(58) Field of Classification Search .................. None
See application file for complete search history.

(56) References Cited

U.S. PATENT DOCUMENTS

2005/0084707 A1* 4/2005 Satsuki et al. ............... 428/690

FOREIGN PATENT DOCUMENTS
WO WO 2006/080640 * 8/2006
* cited by examiner

*Primary Examiner* — D. Lawrence Tarazano
*Assistant Examiner* — Gregory Clark
(74) *Attorney, Agent, or Firm* — McDermott Will & Emery LLP

(57) ABSTRACT

The claimed invention relates to compounds of the formula (I):

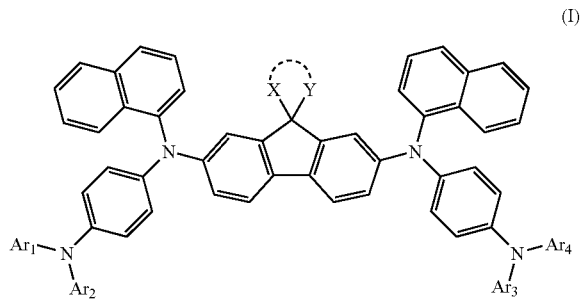

wherein X, Y, $Ar_1$, $Ar_2$, $Ar_3$ and $Ar_4$ are as defined in the specification. The claimed invention also relates to the preparation processes of the said compounds and their uses in the organic electroluminescent device.

17 Claims, 13 Drawing Sheets

AMINE COMPOUNDS, THEIR PREPARATION PROCESSES AND THE ORGANIC ELECTROLUMINESCENT DEVICES USING THE SAME

CROSS-REFERENCE TO RELATED APPLICATIONS

This application is a nonprovisional application which claims priority to Taiwan Application No. 095129292, filed Aug. 10, 2006.

FIELD OF THE INVENTION

The present invention relates to a class of novel amine compounds. The said amine compounds exhibit excellent stability and low oxidative potential, and thus are suitable as the hole injection layer of an organic electroluminescent device. The present invention also relates to an organic electroluminescent device comprising the said amine compounds, wherein the said organic electroluminescent (EL) device may be a display.

BACKGROUND OF THE INVENTION

Cathode Ray Tube (CRT) display was the most convenient display in the world and took a very important position in the display technology. However, due to the rapid development of the optoelectronics industry, the CRT display is gradually replaced by the flat panel displays (FPDs).

The FPDs encompass a growing number of technologies making video displays much lighter and thinner than traditional television and video displays that used CRT. Generally, the FPDs comprise liquid crystal displays, plasma displays, electroluminescent displays, light emitting diode displays, vacuum fluorescent displays, field emission displays, and electrochromic displays, etc. Among the said FPD technologies, organic light-emitting diode displays exhibit characteristics of thin, light weight, self-emission, high brightness, wide viewing angle, rapid response, low power consumption, full-colorization and good flexibility, and therefore are widely deemed as the most potential technology of the next generation of the FPDs.

Based on the materials of the organic films used, the organic light emitting technologies may be mainly classified into two categories: one is small molecule-based organic light emitting system, and the other is polymer-based organic light emitting system. Since the organic light emitting devices exhibit characteristics of light emitting diode (LED), the said small molecule-based organic light emitting system is also referred to organic light-emitting diode (OLED) and the said polymer-based organic light emitting system is also referred to polymer light-emitted diode (PLED).

Typically, an EL device comprises layers of hole injection materials, hole transport materials, electron transport materials, light emitting materials, an anode and a cathode (such as indium tin oxide, i.e., ITO). However, the said materials still need further improvement. For example, the chemical and thermal stability of the said materials should be high enough to render the life of the organic EL device longer.

Since the injection layer is located between the electrode and the transport layer of an organic EL device, it should exhibit excellent electron-injection or hole-injection property. A conventional and typical hole-injection material is a copper phthalocyanine (CuPc) compound, which is an organic molecule comprising eight nitrogen atoms. The said CuPc layer is the first organic layer next to the ITO layer. Moreover, the IP value of the said CuPc layer is 5.0 eV, which is close to the IP value of ITO. Hence, the efficiency of hole-injection of the CuPc layer is pretty good. However, the CuPc film is not completely transparent and may absorb the red light, and therefore the application of the said layer in a full color display has poor performance. Additionally, since the CuPc is easily crystallized, the surface roughness of the layer may be raised when the thickness of the layer is increased, thereby increasing the production of the defects. The other suitable hole injection material is TNATA (IP=5.1 eV, Tg=110° C.), which is commonly used to replace the CuPc material. The said TNATA layer has better transparency than the CuPc layer in the visible spectrum. However, the thermal stability of the TNATA layer needs considerable improvement.

In view of the above, the present invention provides a novel amine compound exhibiting excellent hole-injection property and thermal stability. Moreover, the claimed compounds are suitable for the application in an organic EL device.

SUMMARY OF THE INVENTION

The present invention provides a novel compound of the formula (I):

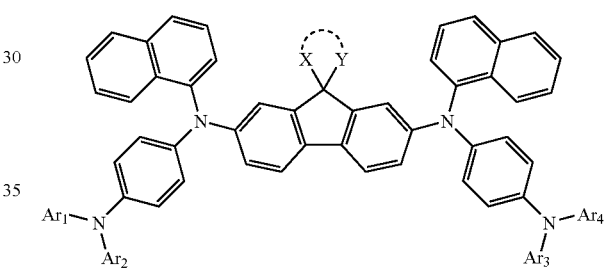

Formula (I)

wherein

X and Y are identical or different, and independently represent straight or branched alkyl, alkenyl, alkynyl, cycloalkyl, alkoxy, halo, amino, nitro, cyano, hydroxyl, heterocyclyl, aryl or heteroaryl group, or X and Y together with C atom to which they are attached form an optionally substituted saturated or unsaturated cyclohydrocarbon, heterocyclic ring, aryl ring, heteroaryl ring, benzene ring-fused cyclic hydrocarbon, fused benzene ring-fused cyclic hydrocarbon, benzoheterocyclic ring, fused benzene rings-fused heterocyclic ring or polyheterocyclic ring; and $Ar_1$, $Ar_2$, $Ar_3$ and $Ar_4$ are identical or different, and represent optionally substituted aryl groups.

The present invention also relates to the preparation processes of the said compounds and their uses in the organic EL device.

BRIEF DESCRIPTION OF THE DRAWINGS

The drawings are included to provide a further understanding of the claimed invention, and are incorporated in and constitute a part of this specification. The drawings illustrate embodiments of the invention and, together with the specification, serve to explain the principle of the invention. In the drawings.

DESCRIPTION OF THE SPECIFIC EMBODIMENTS

Figure 1:
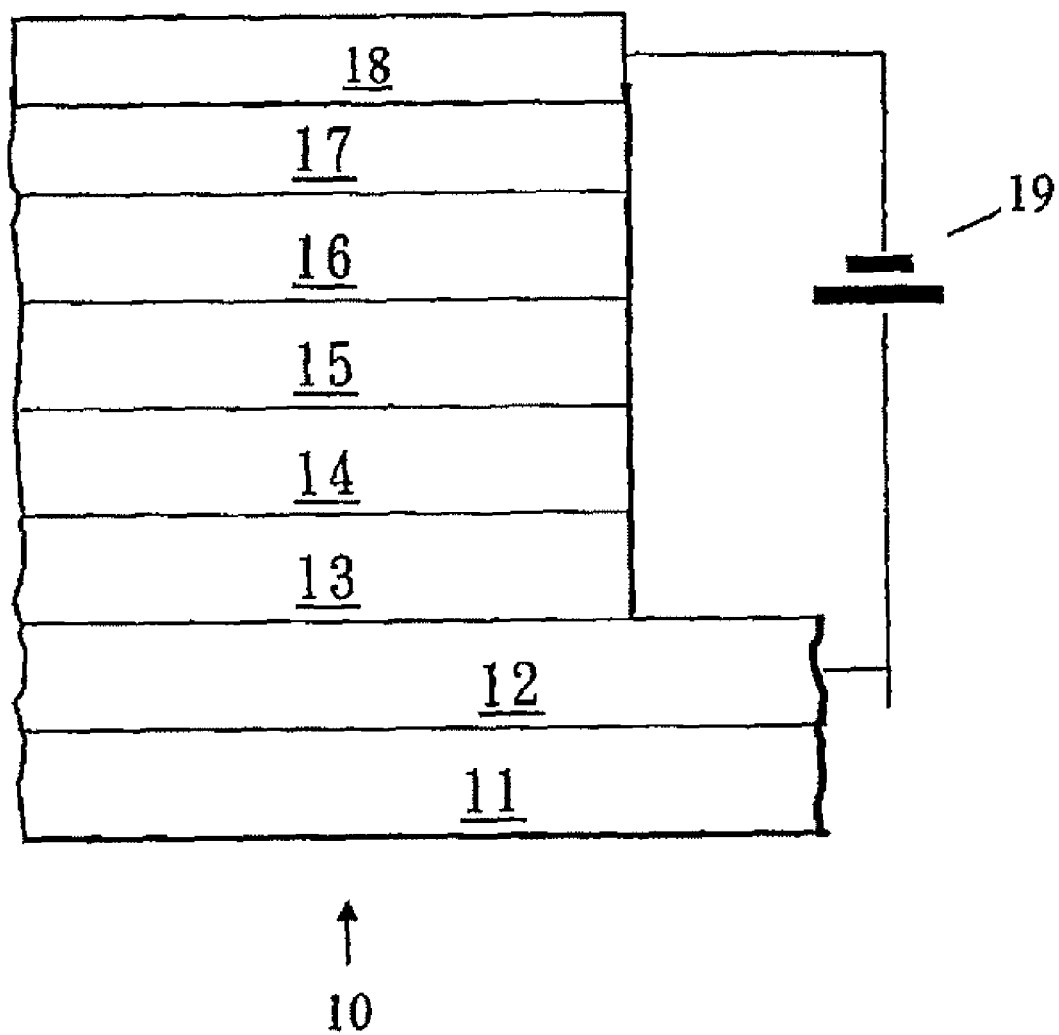
FIG. 1 is the schematic view of the structure of an exemplary embodiment of the organic EL device.
Figure 2:
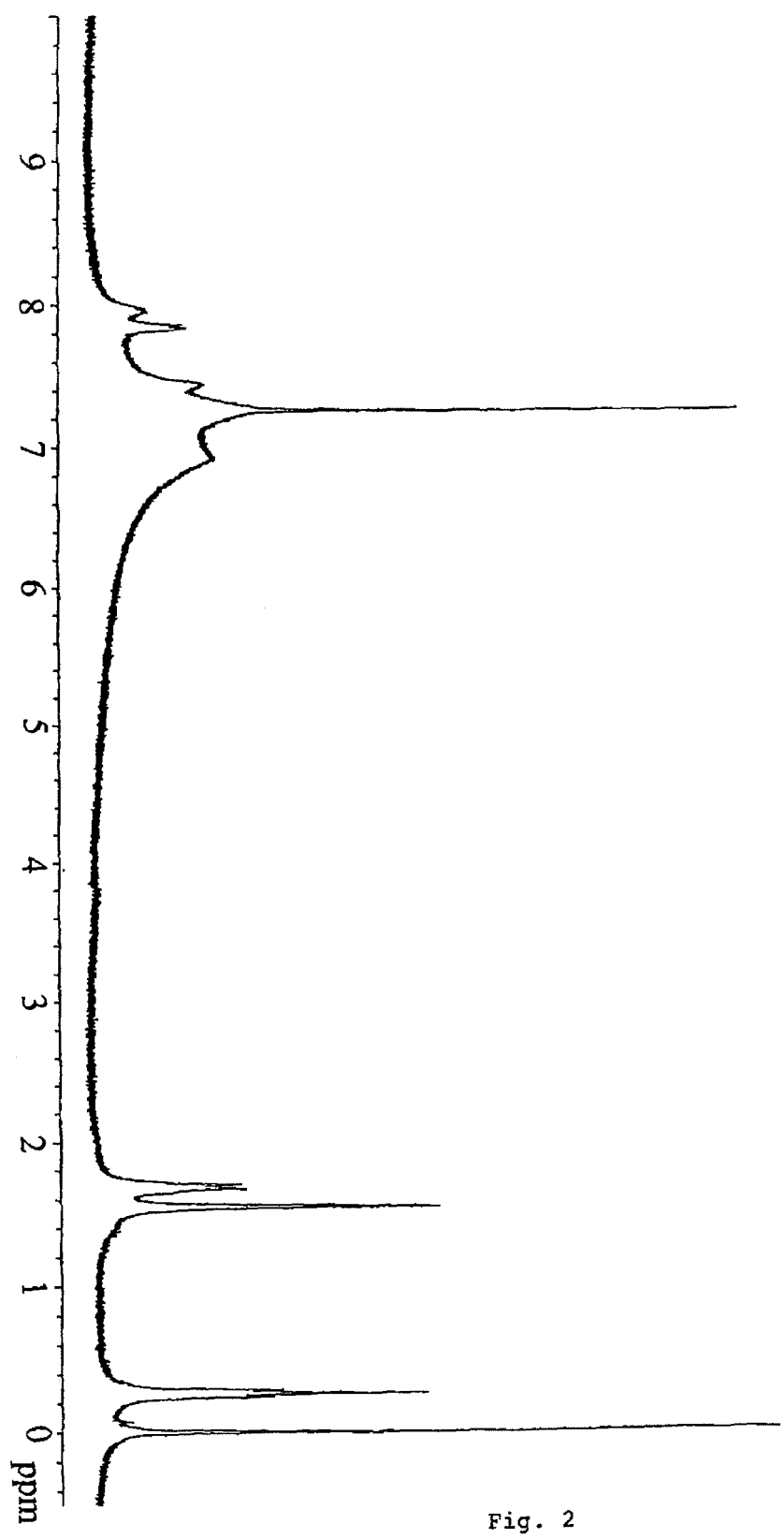
FIG. 2 is the NMR spectrum of the compound S701 of the present invention.
Figure 3:
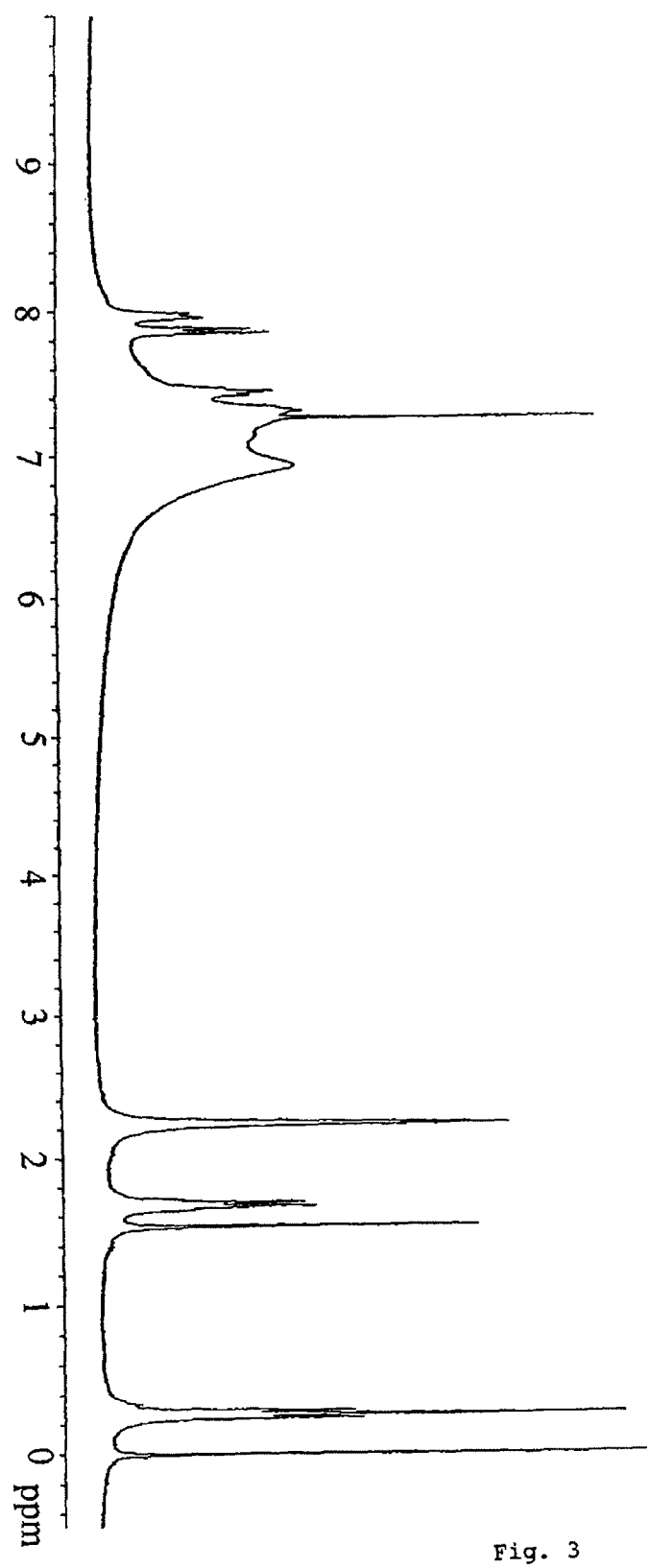
FIG. 3 is the NMR spectrum of the compound S702 of the present invention.
Figure 4:
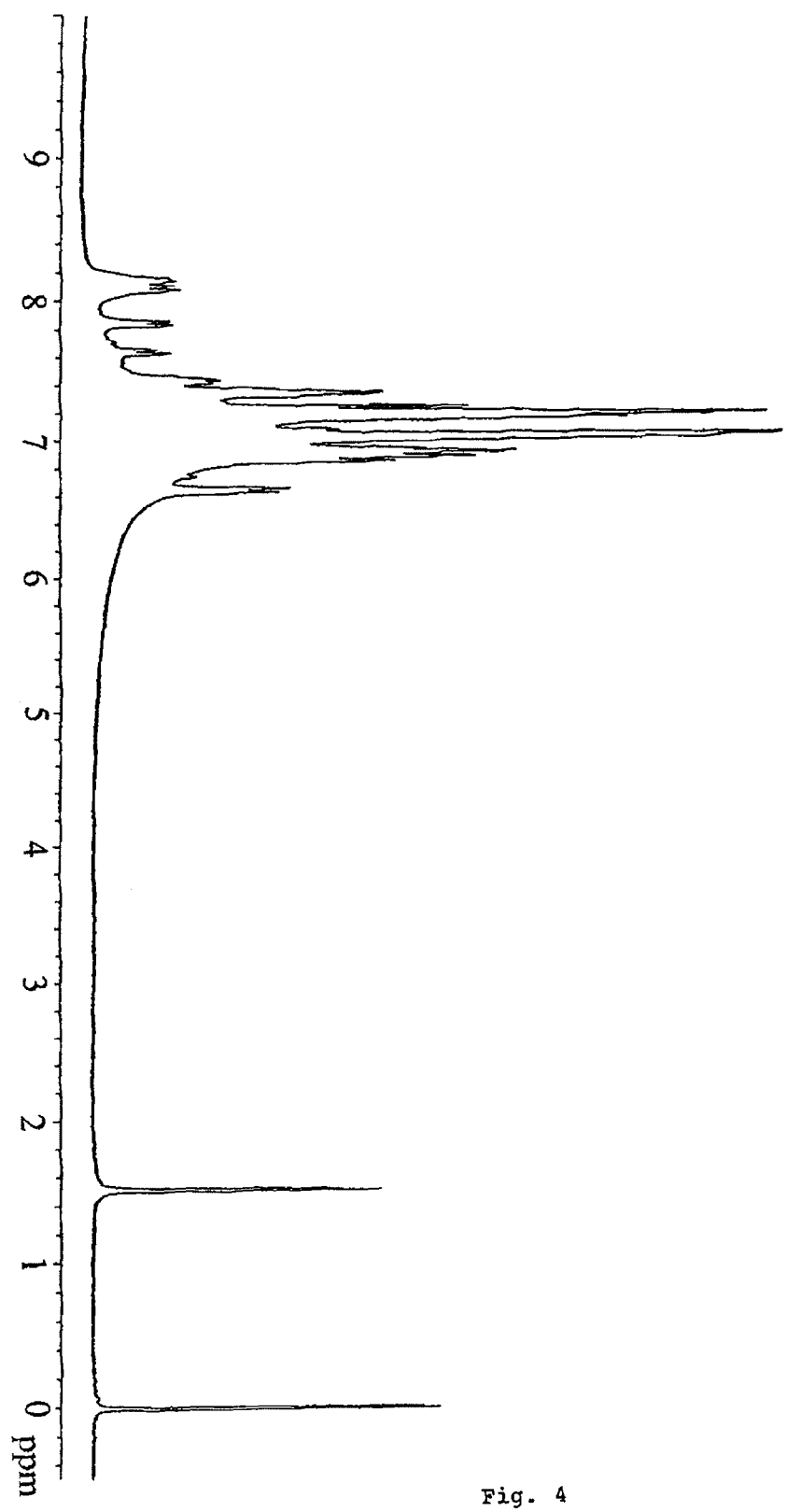
FIG. 4 is the NMR spectrum of the compound S703 of the present invention.
Figure 5:
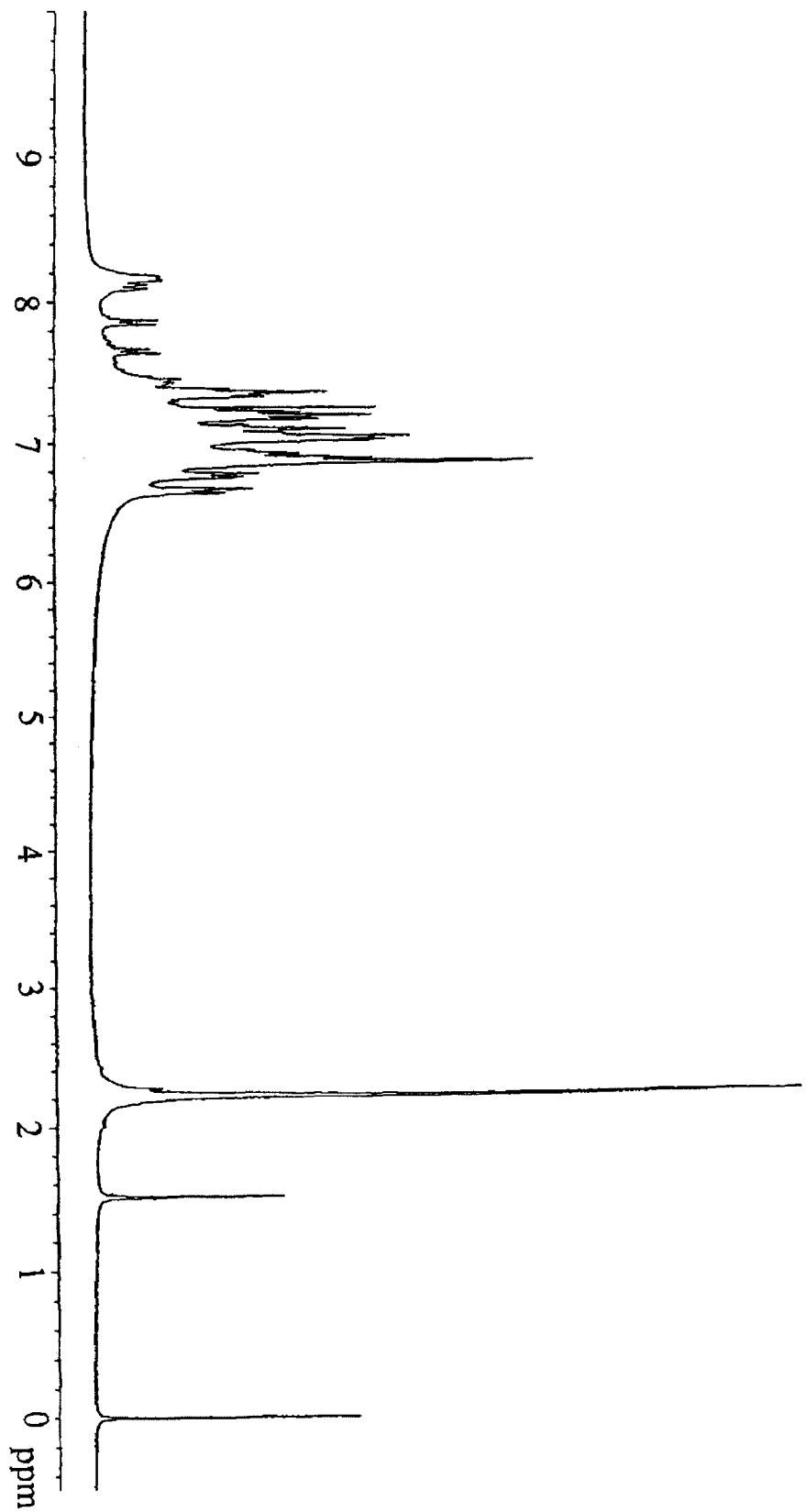
FIG. 5 is the NMR spectrum of the compound S704 of the present invention.
Figure 6:
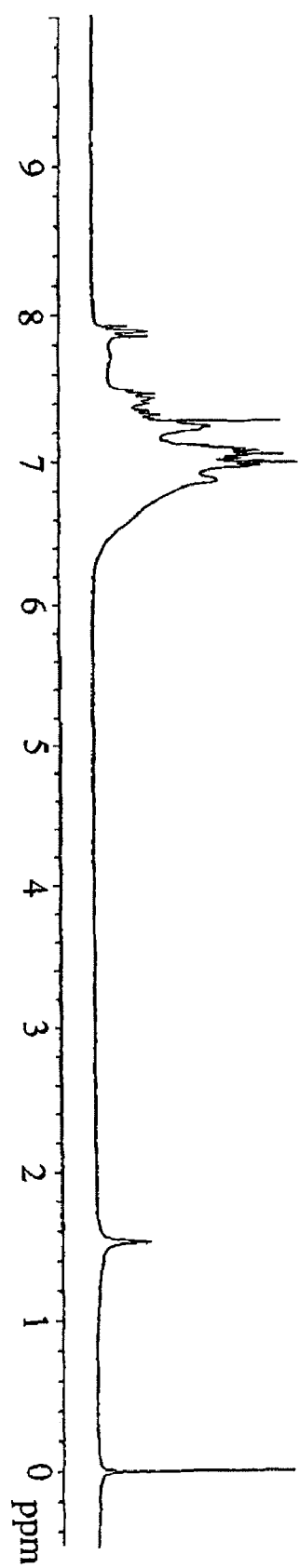
FIG. 6 is the NMR spectrum of the compound S706 of the present invention.
Figure 7:
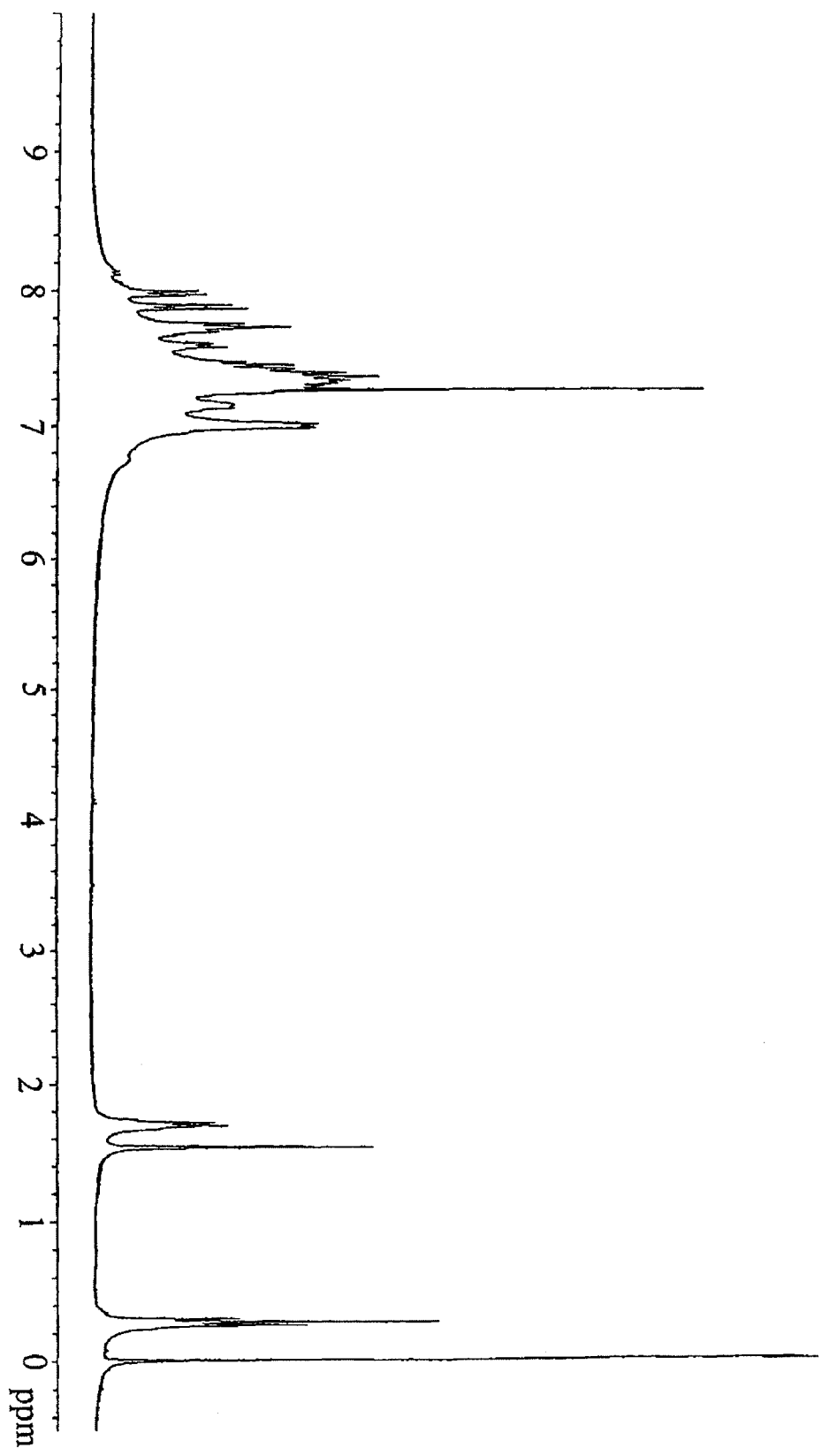
FIG. 7 is the NMR spectrum of the compound S708 of the present invention.
Figure 8:
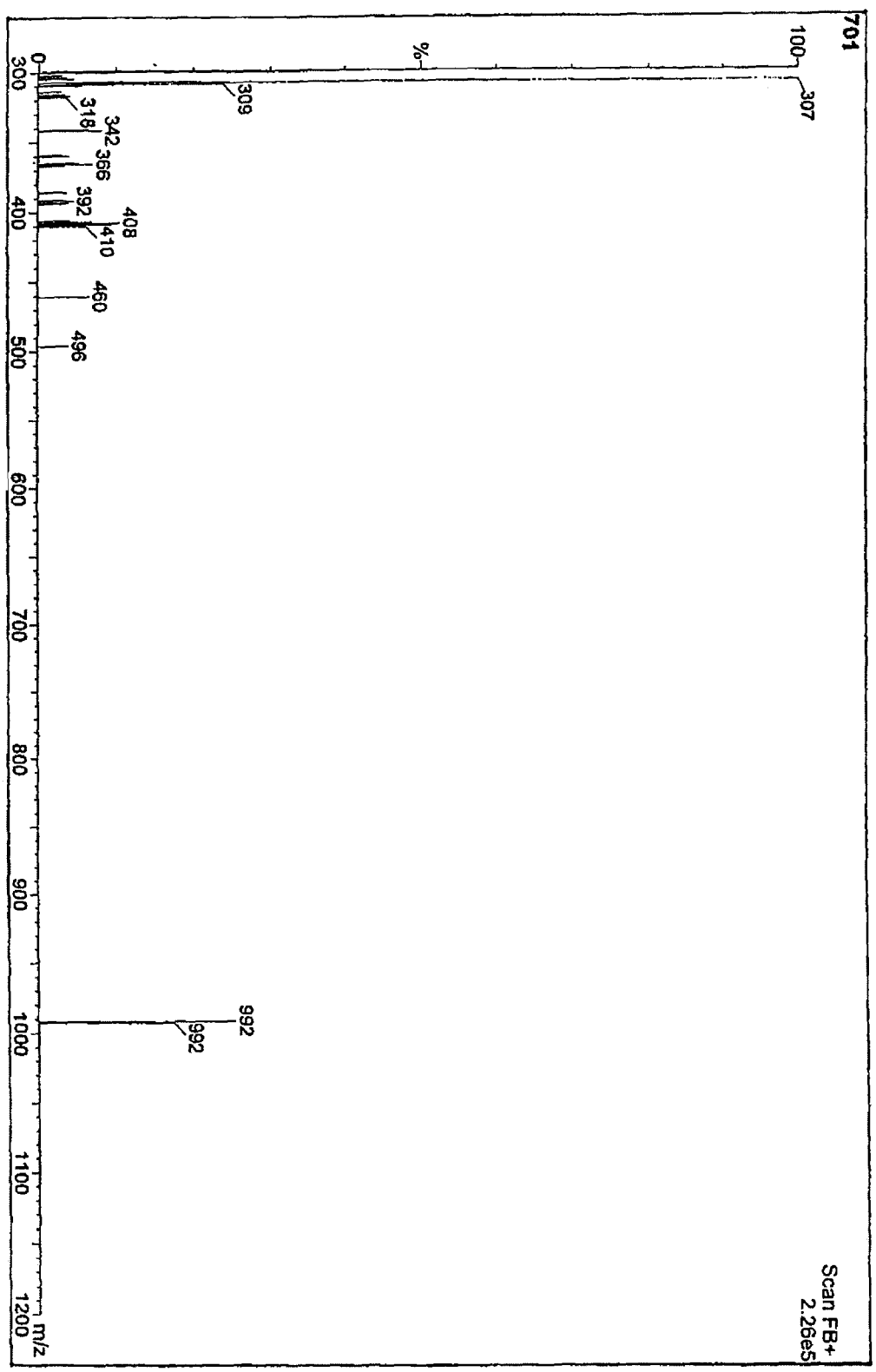
FIG. 8 is the MS spectrum of the compound S701 of the present invention.
Figure 9:
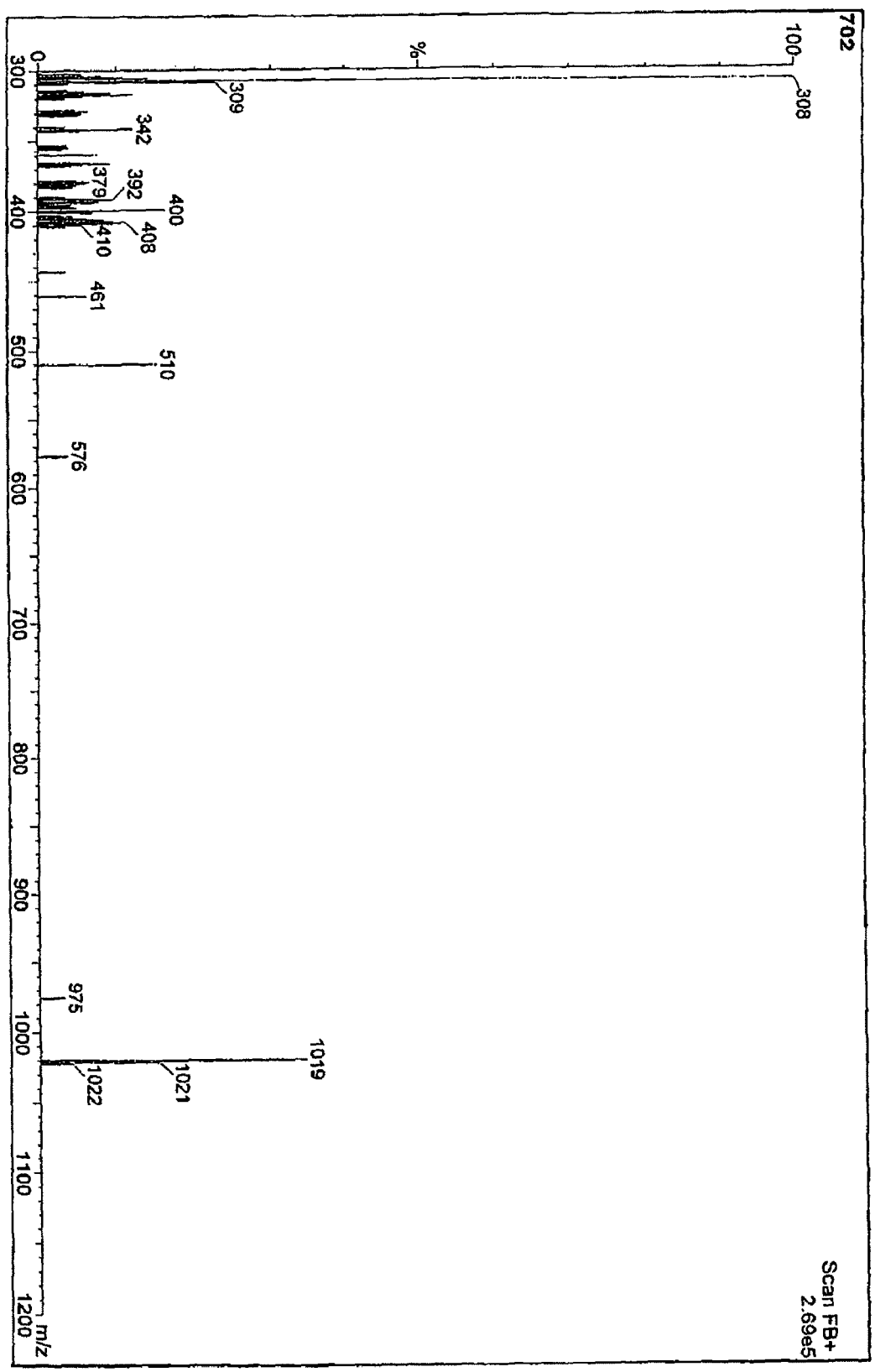
FIG. 9 is the MS spectrum of the compound S702 of the present invention.
Figure 10:
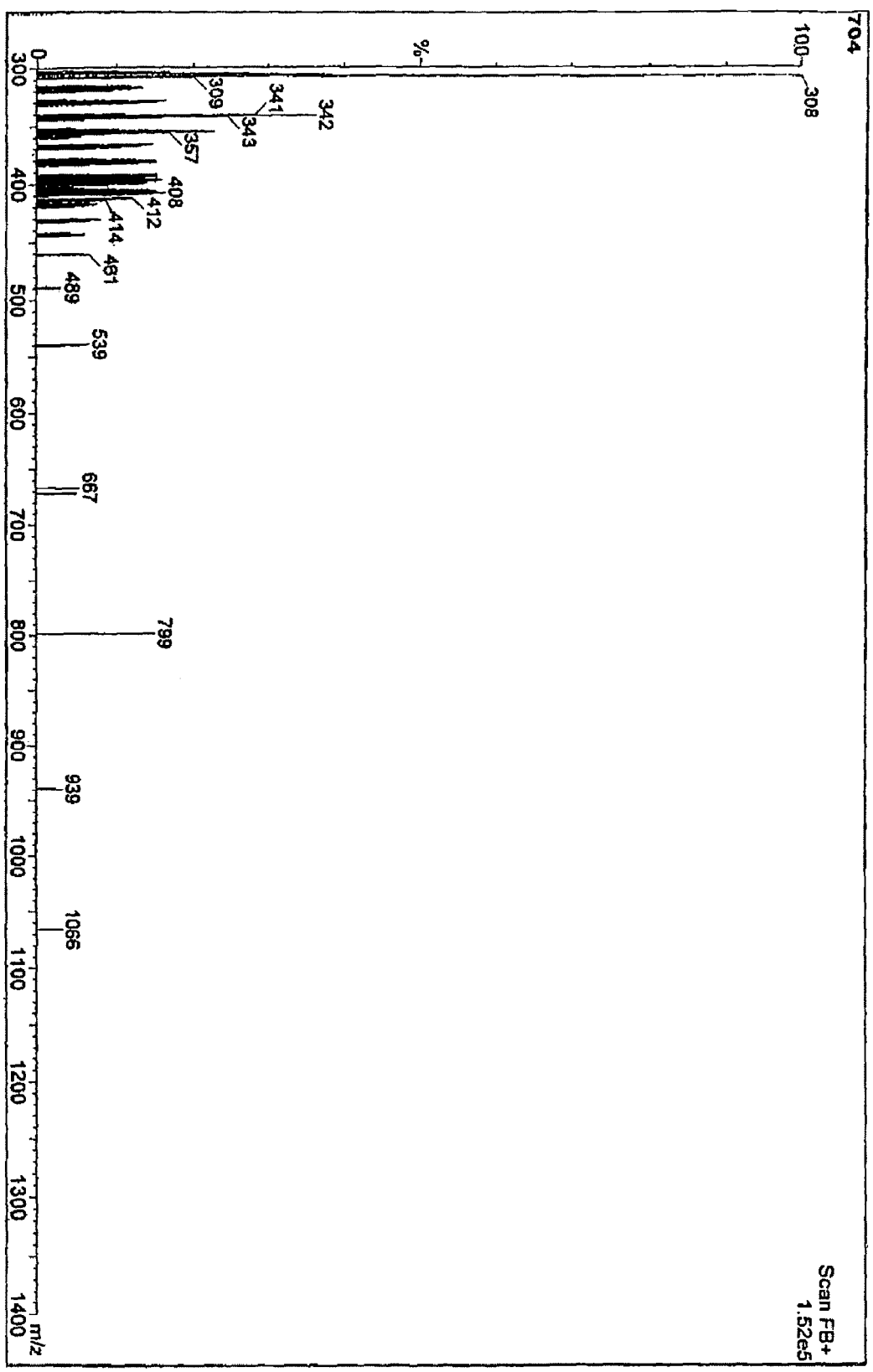
FIG. 10 is the MS spectrum of the compound S704 of the present invention.
Figure 11:
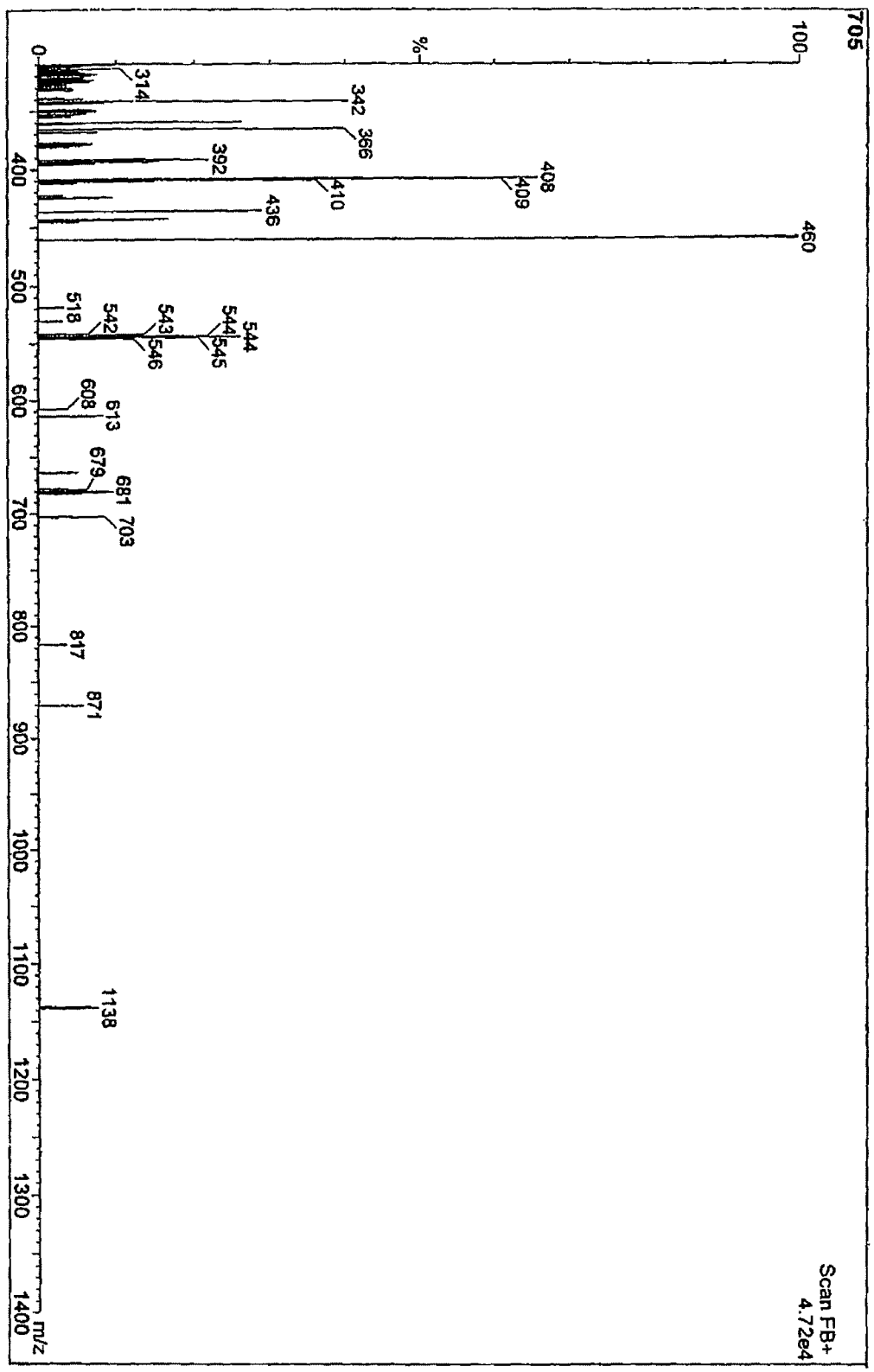
FIG. 11 is the MS spectrum of the compound S705 of the present invention.
Figure 12:
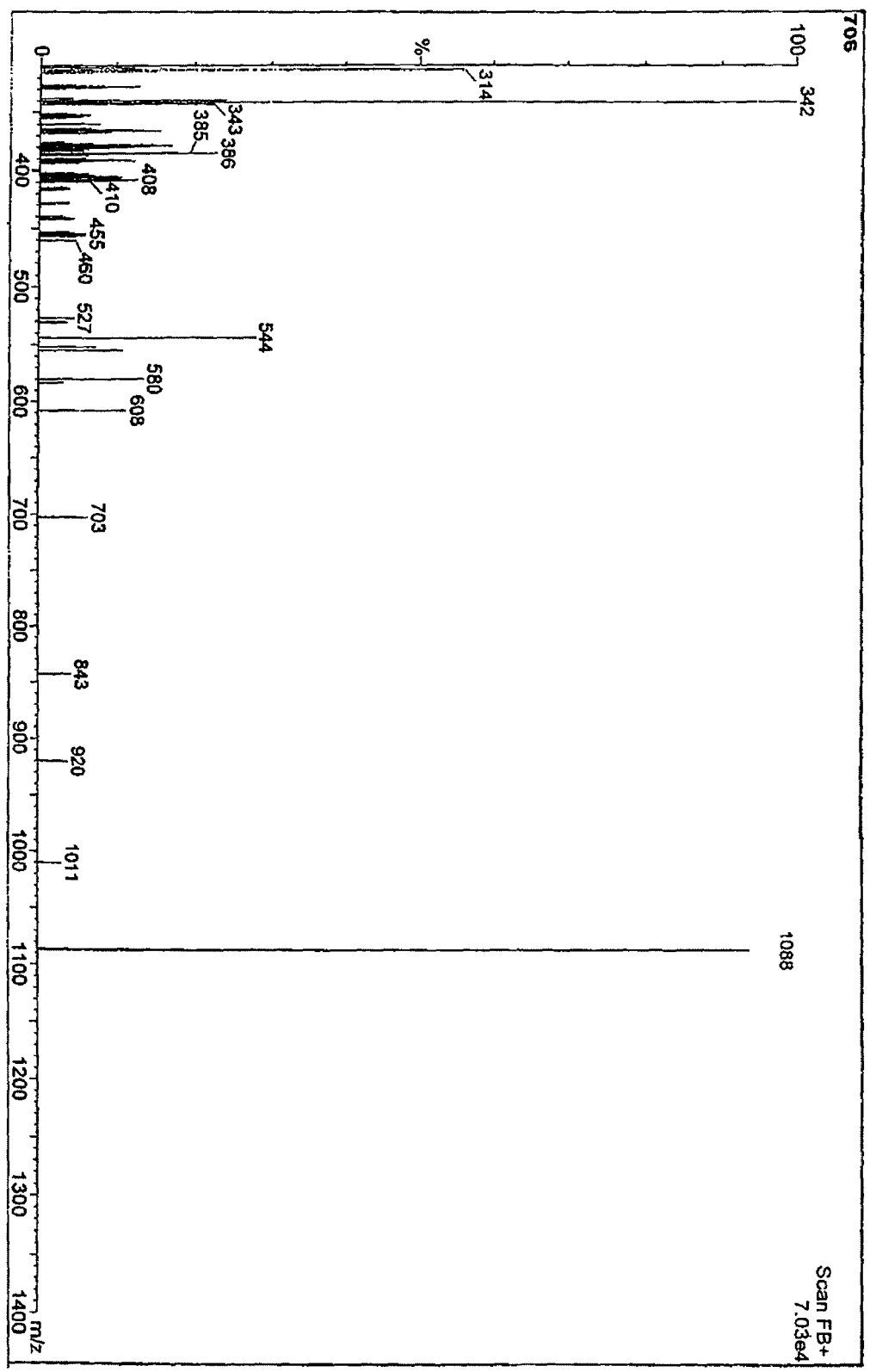
FIG. 12 is the MS spectrum of the compound S706 of the present invention.
Figure 13:
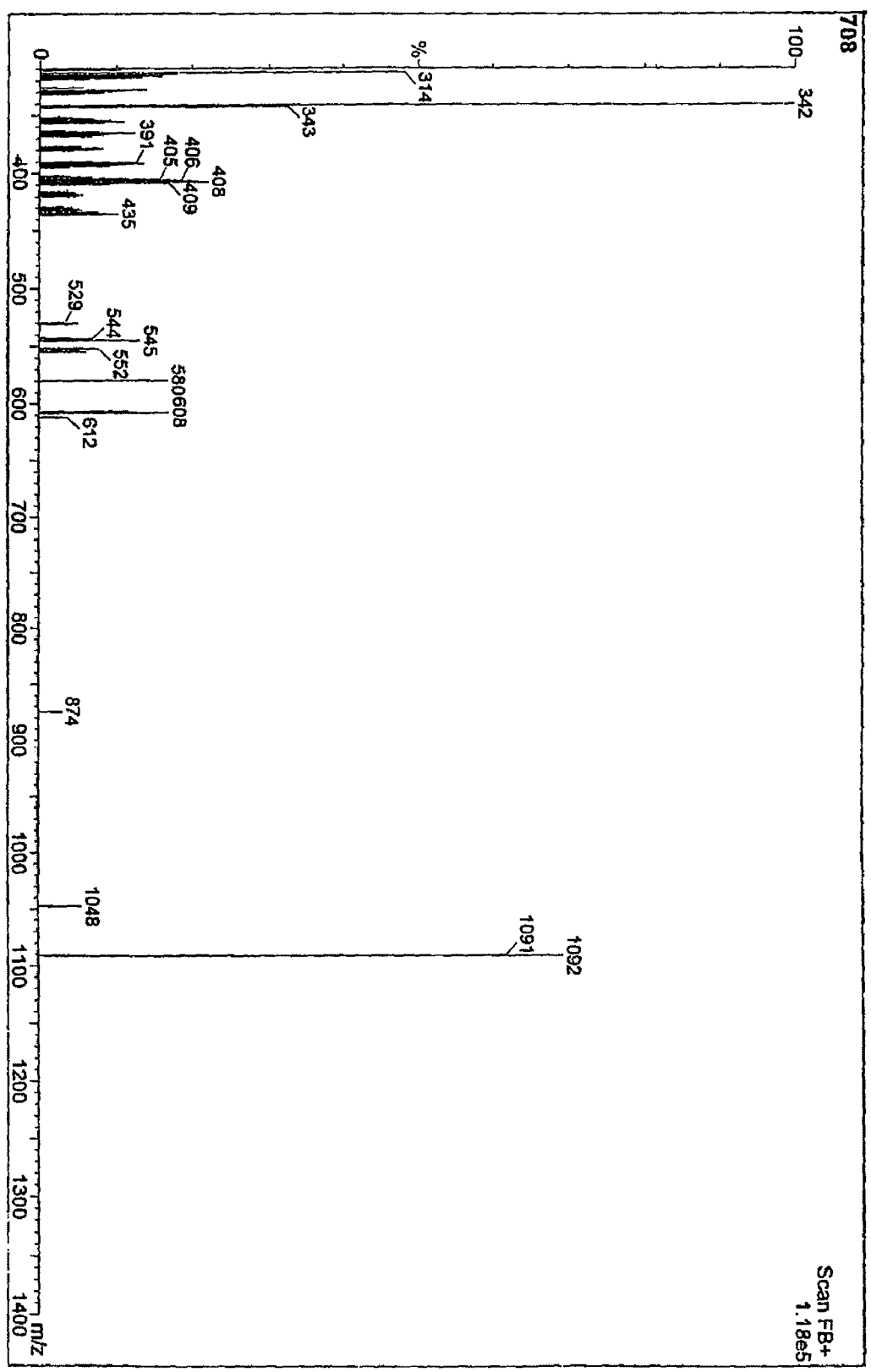
FIG. 13 is the MS spectrum of the compound S708 of the present invention.

As used in this description and the accompanying claims, the term "alkyl" shall refer to a linear or branched saturated hydrocarbon radical. Examples of alkyl groups are methyl, ethyl, propyl, isopropyl, butyl, isobutyl, sec-butyl, tert-butyl, pentyl, neopentyl, sec-pentyl, isopentyl, tert-pentyl or hexyl.

The term "alkenyl" shall refer to an unsaturated hydrocarbon radical having one or more carbon-carbon double bond(s) and all the isomers thereof. Examples of alkenyl groups are ethenyl, propenyl, butenyl, pentenyl or hexenyl.

The term "alkynyl" shall refer to an unsaturated hydrocarbon radical having one or more carbon-carbon triple bond(s) and all the isomers thereof. Examples of alkynyl are ethynyl, propynyl, butynyl or pentynyl.

The term "cycloalkyl" shall refer to a cyclic alkyl radical having 3 or more carbon atoms. Examples of cycloalkyl groups are cyclopropyl, cyclobutyl, cyclopentyl, cyclohexyl or cycloheptyl.

The term "alkoxy" shall refer to a linear or branched alkyl radical linked to oxygen. Examples of alkoxy groups are methoxy, ethoxy, propoxy or butoxy.

The term "halo" means a radical of the nonmetallic elements of the seventh group of periodic table. Examples of halo groups are fluoro, chloro, bromo or iodo.

The term "heterocyclic ring" means a saturated or partially-saturated mono-cyclic ring system in which at least one carbon atom is replaced by a heteroatom selected from a group consisting of O, S and N. Examples of saturated heterocyclic ring groups are pyrrolidine, imidazolidine, pyrazolidine, tetrahydrofuran, dioxane, piperidine, piperazine, morpholine, thiomorpholine, tetrahydrothiophene, tetrahydro-2H-pyran or dithiane. Examples of partially-saturated heterocyclic ring groups are oxazolidine, isoxazolidine, imidazoline, pyrazoline, 1,2,3,6-tetrapyridine or 3,6-dihydro-2H-pyran.

The term "aryl" means an organic radical derived from an aromatic hydrocarbon. Examples of aryl groups are phenyl or nephthyl.

The term "heteroaryl" means an aryl ring in which at least one carbon atom is replaced by a heteroatom selected from a group consisting of O, S and N. Examples of heteroaryl groups are pyrrolyl, imidazolyl, pyrazolyl, oxadiazolyl, isoxazolyl, thiazinyl, furanyl, thiophenyl, pyridyl, pyridazinyl, pyrimidinyl or azepinyl.

The term "cyclohydrocarbon" means a cyclic alkane having 3 or more carbon atoms. Examples of cyclohydrocarbon groups are cyclopropane, cyclobutane, cyclopentane, cyclohexane or cycloheptane.

The term "fused benzene ring" means a polycyclic group composed of two or more benzene rings fused together. Examples of fused benzene ring are naphthalene, anthracene, phenanthrene, chrysene or picene.

The term "benzene ring-fused cyclic hydrocarbon" means a polycyclic system composed of one or more benzene ring fused with one or more cyclic hydrocarbon. Examples of benzene ring-fused cyclic hydrocarbon are fluorine, indene or dihydroindene.

The term "fused benzene ring-fused cyclic hydrocarbon" means a polycyclic system composed of one or more fused benzene ring fused with one or more cyclic hydrocarbon. Example of fused benzene ring-fused cyclic hydrocarbon is acenaphthylene.

The term "benzene ring-fused heterocyclic ring" means a polycyclic system composed of one or more benzene ring fused with one or more heterocyclic ring. Examples of benzene ring-fused heterocyclic ring are benzofuran, benzothiophene, benzopyrrole, indole, quinoline, isoquinoline, dibenzofuran, dibenzothiophene, dibenzopyrrole, carbazole or acridine.

The term "fused benzene ring-fused heterocyclic ring" means a polycyclic system composed of one or more fused benzene ring fused with one or more heterocyclic ring. Examples of fused benzene ring-fused heterocyclic ring are naphtho[2,3-6]thiophene or phenanthroline.

The term "polyheterocyclic ring" means a polycyclic system composed of two or more heterocyclic rings. Examples of polyheterocyclic ring are purine, guanine or caffeine.

According to an embodiment of the present invention, X and Y are identical or different, and represent straight or branched $C_{1-20}$alkyl, $C_{2-20}$alkenyl, $C_{2-20}$alkynyl, $C_{3-20}$cycloalkyl, $C_{1-20}$alkoxy, halo, amino, nitro, cyano, hydroxyl, $C_{3-20}$heterocyclyl, $C_{3-20}$aryl or $C_{3-20}$heteroaryl group, or X and Y together with C atom to which they are attached form an optionally substituted saturated or unsaturated $C_{3-20}$cyclohydrocarbon, $C_{3-20}$heterocyclic ring, $C_{3-20}$aryl ring, $C_{3-20}$heteroaryl ring, benzene ring-fused $C_{3-20}$cyclic hydrocarbon, fused benzene ring-fused $C_{3-20}$cyclic hydrocarbon, benzo $C_{3-20}$heterocyclic ring, fused benzene rings-fused $C_{3-20}$heterocyclic ring or polyheterocyclic ring; $Ar_1$, $Ar_2$, $Ar_3$ and $Ar_4$ are identical or different, and represent same or different optionally substituted $C_{3-20}$aryl groups.

According to another embodiment of the present invention, X and Y are identical or different, and represent straight or branched $C_{1-6}$alkyl, $C_{2-6}$alkenyl, $C_{2-6}$alkynyl, $C_{3-8}$cycloalkyl, $C_{1-6}$alkoxy, halo, amino, nitro, cyano, hydroxyl, $C_{3-8}$heterocyclyl, $C_{3-8}$aryl or $C_{3-8}$heteroaryl group, or X and Y together with C atom to which they are attached form an optionally substituted saturated or unsaturated $C_{3-8}$cyclohydrocarbon, $C_{3-8}$heterocyclic ring, $C_{3-8}$aryl ring, $C_{3-8}$heteroaryl ring, benzene ring-fused $C_{3-8}$cyclic hydrocarbon, fused benzene rings-fused $C_{3-8}$cyclic hydrocarbon, benzo$C_{3-8}$heterocyclic ring, fused benzene ring-fused $C_{3-8}$heterocyclic ring or polyheterocyclic ring; $Ar_1$, $Ar_2$, $Ar_3$ and $Ar_4$ are identical or different, and represent optionally substituted $C_{3-8}$aryl groups.

According to another embodiment of the present invention, X and Y are identical or different, and independently represent straight or branched $C_{1-6}$alkyl, $C_{2-6}$alkenyl, $C_{2-6}$alkynyl, $C_{3-8}$cycloalkyl, $C_{1-6}$alkoxy, halo, amino, nitro, cyano, hydroxyl, $C_{3-8}$heterocyclyl, $C_{3-8}$aryl or $C_{3-8}$heteroaryl group, or X and Y together with C atom to which they are attached form an optionally substituted saturated or unsaturated $C_{3-8}$cyclohydrocarbon, $C_{3-8}$aryl ring, benzene ring-fused $C_{3-8}$cyclic hydrocarbon or fused benzene rings-fused $C_{3-8}$cyclic hydrocarbon; $Ar_1$, $Ar_2$, $Ar_3$ and $Ar_4$ are identical or different, and represent optionally substituted $C_{3-8}$aryl groups.

According to another embodiment of the present invention, X and Y are identical or different, and represent same or different straight or branched $C_{1-6}$alkyl or $C_{3-8}$aryl, or X and Y together with C atom to which they are attached form an optionally substituted saturated or unsaturated benzene ring-fused $C_{3-8}$cyclic hydrocarbon or fused benzene rings-fused $C_{3-8}$cyclic hydrocarbon; $Ar_1$, $Ar_2$, $Ar_3$ and $Ar_4$ are identical or different, and represent optionally substituted $C_{3-8}$aryl groups.

According to a preferred embodiment of the present invention, X and Y independently represent methyl or ethyl.

According to a preferred embodiment of the present invention, X and Y may together with C atom to which they are attached form an optionally substituted benzocyclopentane.

According to a preferred embodiment of the present invention, $Ar_1$, $Ar_2$, $Ar_3$ and $Ar_4$ are identical or different, and represent optionally substituted phenyl.

According to a preferred embodiment of the present invention, $Ar_1$, $Ar_2$, $Ar_3$ and $Ar_4$ are identical or different, and represent phenyl or tolyl.

According to a preferred embodiment of the present application, the compounds of the claimed invention are directed to the compounds of the formula (II)

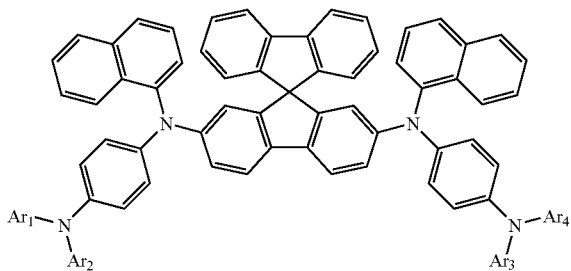

Formula (II)

wherein $Ar_1$, $Ar_2$, $Ar_3$ and $Ar_4$ are identical or different, and represent optionally substituted $C_{3-20}$aryl groups.

According to a preferred embodiment of the present application, the compounds of the claimed invention are directed to the compounds of the formula (III)

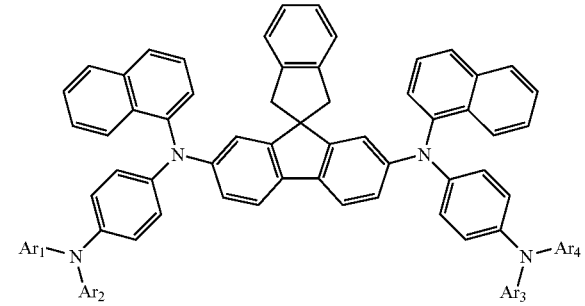

Formula (III)

wherein $Ar_1$, $Ar_2$, $Ar_3$ and $Ar_4$ are identical or different, and represent optionally substituted $C_{3-20}$aryl groups.

According to a preferred embodiment of the present application, the compounds of the claimed invention are directed to the compounds of the formula (IV)

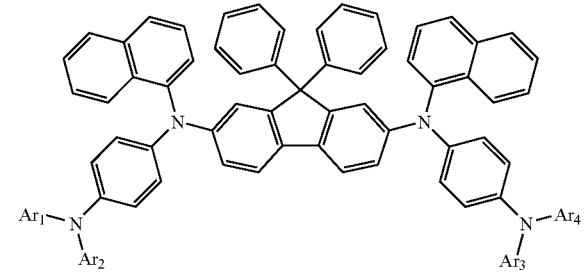

Formula (IV)

wherein $Ar_1$, $Ar_2$, $Ar_3$ and $Ar_4$ are identical or different, and represent optionally substituted $C_{3-20}$aryl groups.

According to another preferred embodiment of the present application, the compounds of the claimed invention are directed to the compounds of the formula (V)

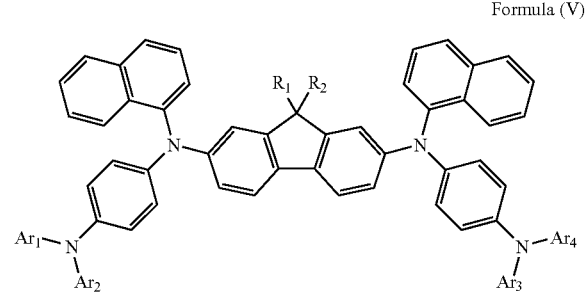

Formula (V)

wherein $R_1$ and $R_2$ are identical or different, and represent $C_{1-6}$alkyl, and $Ar_1$, $Ar_2$, $Ar_3$ and $Ar_4$ are identical or different, and represent optionally substituted $C_{3-20}$aryl groups.

According to a more preferred embodiment of the present invention, the compounds of the claimed invention are directed to the following compounds:
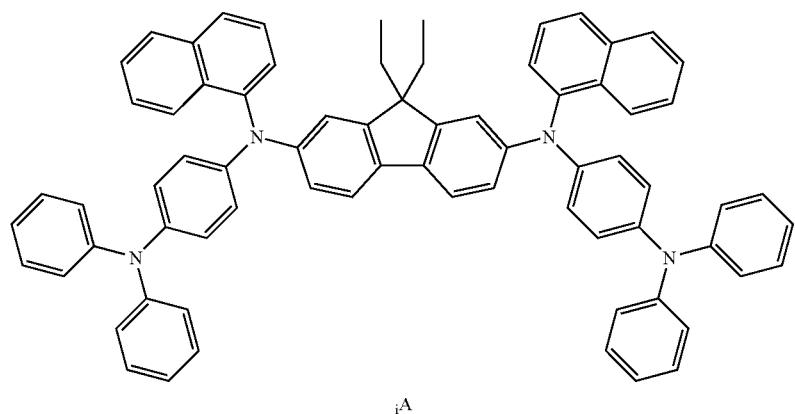
S701
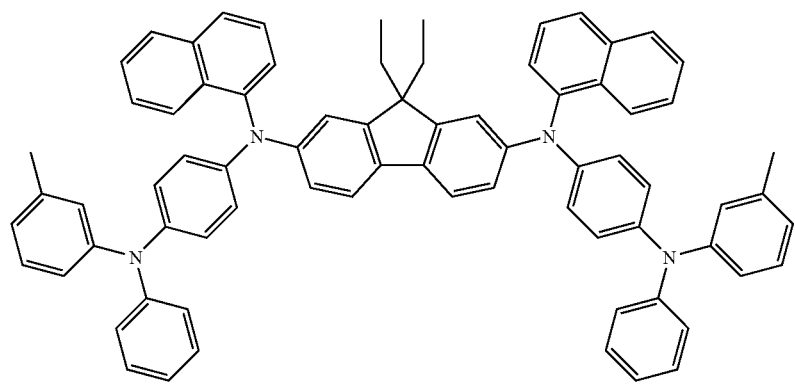
S702
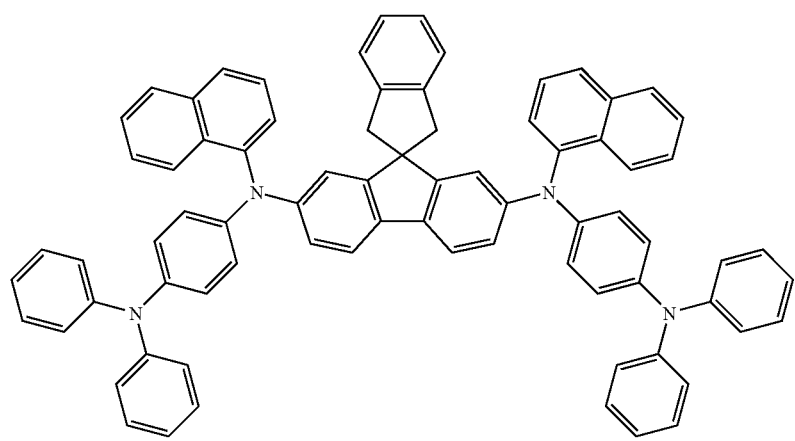
S703

S704
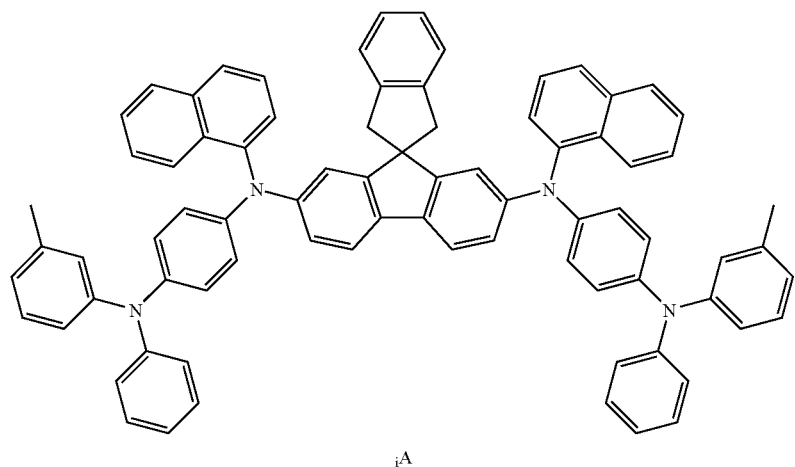
S705
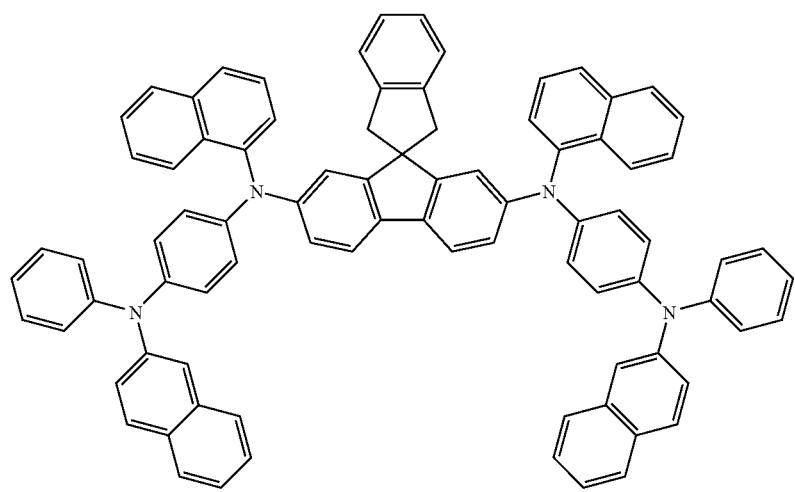
S706
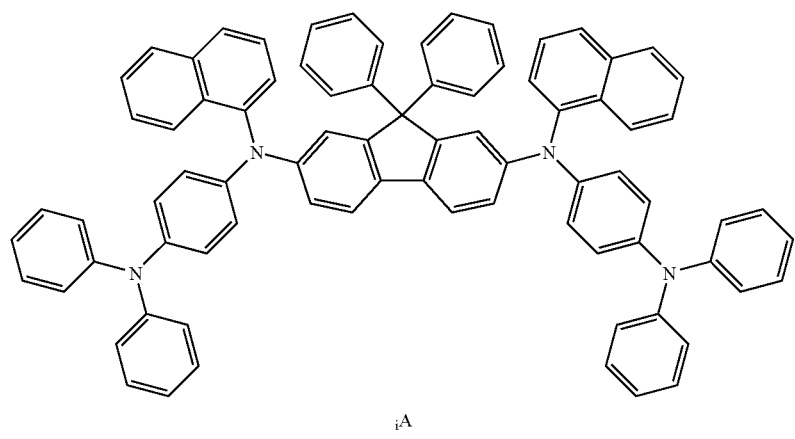

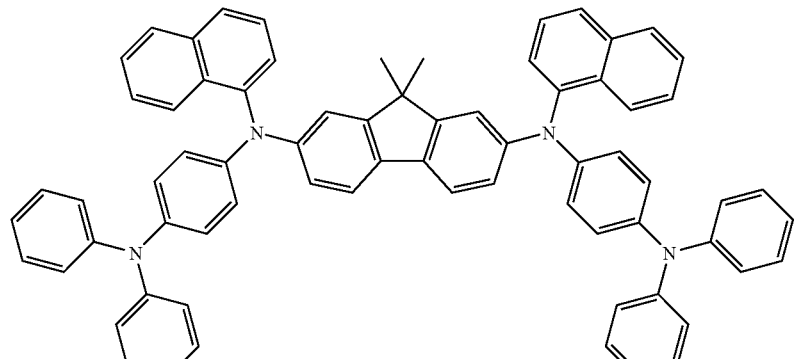
S710
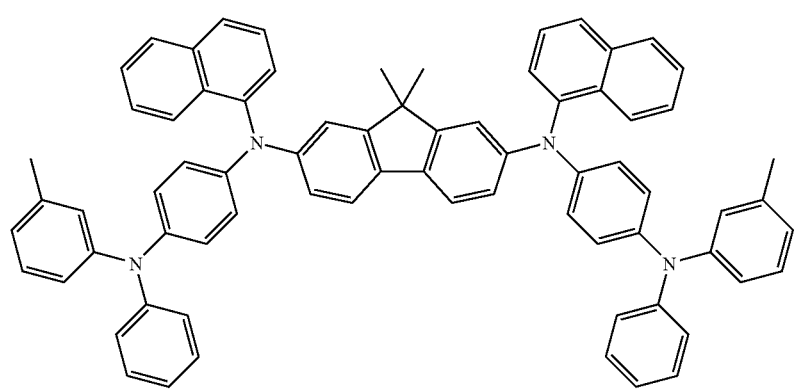
S707
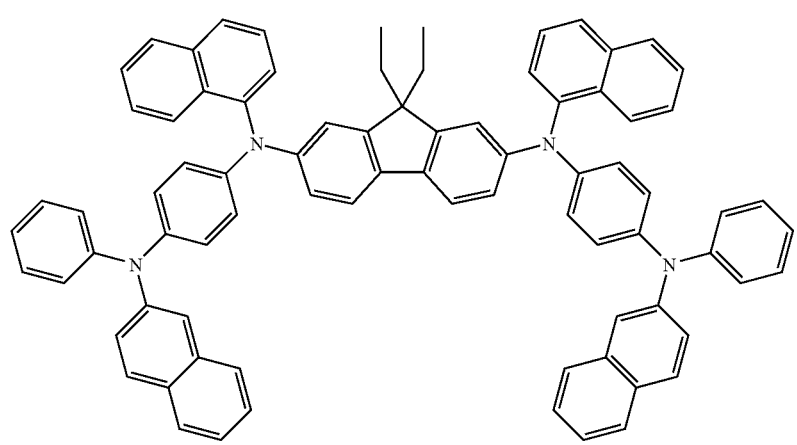
S708

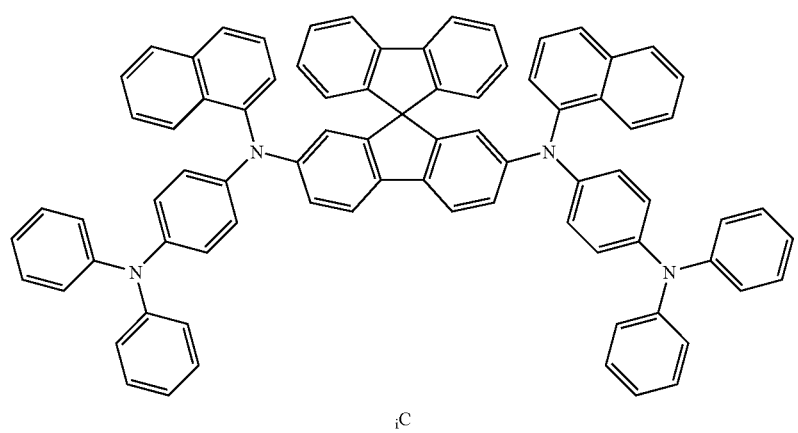

iC

The invention also includes all suitable isotopic variations of a compound of the claimed invention. An isotopic variation of a compound of the claimed invention is defined as the replacement of at least one atom with the one having the same atomic number but an atomic weight different from the naturally occurring atom. Examples of isotopes that can be incorporated into compounds of the claimed invention include isotopes of hydrogen, carbon, nitrogen, oxygen, phosphorus, sulfur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$. Isotopic variations of the compounds of the claimed invention may generally be prepared by conventional procedures such as the preparations described hereafter using appropriate isotopic variations of suitable reagents.

The present invention also relates to a preparation process of the compounds of the formula (I)

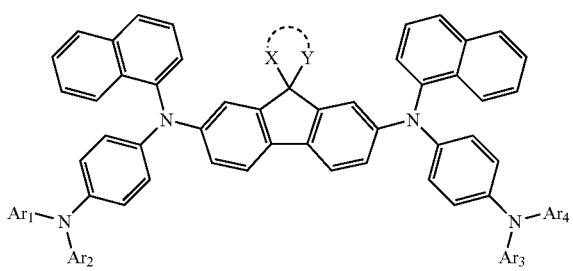

Formula (I)

wherein

X and Y are identical or different, and represent straight or branched alkyl, alkenyl, alkynyl, cycloalkyl, alkoxy, halo, amino, nitro, cyano, hydroxyl, heterocyclyl, aryl or heteroaryl group, or X and Y together with C atom to which they are attached form an optionally substituted saturated or unsaturated cyclohydrocarbon, heterocyclic ring, aryl ring, heteroaryl ring, benzene ring-fused cyclic hydrocarbon, fused benzene ring-fused cyclic hydrocarbon, benzoheterocyclic ring, fused benzene rings-fused heterocyclic ring or polyheterocyclic ring; and $Ar_1$, $Ar_2$, $Ar_3$ and $Ar_4$ are identical or different, and represent same or different optionally substituted aryl groups.

The compounds of the formula (I) may be prepared by the following procedures.

First, suitable amounts of the compound (A)

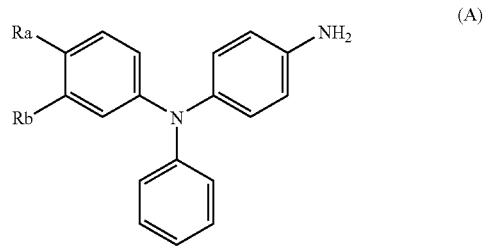

(A)

wherein

Ra and Rb are independently selected from the group consisting of hydrogen, straight or branched alkyl, alkenyl or alkynyl, cycloalkyl, alkoxy, halo, amino, nitro, cyano, hydroxyl, heterocyclyl, aryl and heteroaryl; preferably, Ra and Rb independently are hydrogen, straight or branched $C_{1-10}$alkyl, $C_{1-10}$alkenyl or $C_{1-10}$alkynyl, $C_{1-10}$alkoxy or phenyl; more preferably, Ra and Rb independently are hydrogen, straight or branched $C_{1-6}$alkyl or phenyl; or Ra and Rb together with C atom to which they are attached form an optionally substituted saturated or unsaturated cyclohydrocarbon, heterocyclic ring, aryl ring, heteroaryl ring, benzene ring-fused cyclic hydrocarbon, fused benzene ring-fused cyclic hydrocarbon, benzoheterocyclic ring, fused benzene rings-fused heterocyclic ring or polyheterocyclic ring; preferably, Ra and Rb together with C atom to which they are attached form an aryl ring; more preferably, the said aryl ring is phenyl or naphthyl ring;

and compound (B)

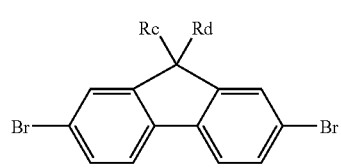

(B)

wherein

Rc and Rd are independently selected from the group consisting of hydrogen, straight or branched alkyl, alkenyl or alkynyl, cycloalkyl, alkoxy, halo, amino, nitro, cyano, hydroxyl, heterocyclyl, aryl and heteroaryl; or Rc and Rd together with C atom to which they are attached form an optionally substituted saturated or unsaturated cyclohydrocarbon, heterocyclic ring, aryl ring, heteroaryl ring, benzene ring-fused cyclic hydrocarbon, fused benzene ring-fused cyclic hydrocarbon, benzoheterocyclic ring, fused benzene rings-fused heterocyclic ring or polyheterocyclic ring;

and suitable amounts of nitrobenzene and potassium carbonate were added into a suitable container. Subsequently, a suitable amount of copper powder was added under inert gas such as nitrogen gas, then the reaction was heated and stirred. After the reaction completed, a suitable amount of 1-bromonaphthalene was added and the reaction was continued until the complete production of the product. After cooling, the reaction was extracted by a suitable solvent, followed by removal of the said solvent by a conventional process and purification to obtain the compound of the invention.

The aforementioned preparation process may be summarized by the following reaction equation:

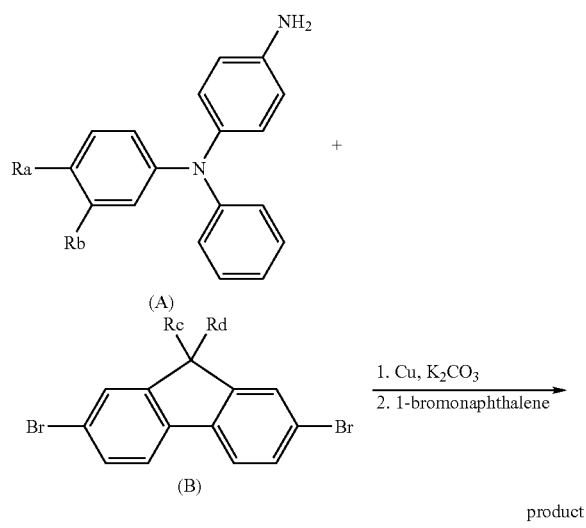

The present invention also relates to an organic EL device, wherein the said device comprises the compound of the formula (I).

According to an embodiment of the present invention, the said compound of the formula (I) is used as the hole-injection layer of an organic EL device.

The present invention may be applied in various device structures, wherein the essential elements of the said device are an anode, a cathode, a hole-transporting layer and a light-emitting layer. FIG. 1 shows a typical layout schema of the said device, which comprises a substrate 11, an anode 12, an optional hole-injection layer 13, a hole-transporting layer 14, a light-emitting layer 15, electron-transporting layer 16, an electron-injection layer 17, a metal cathode 18 and an electric power source 19. The materials used in the said layers are described below. It should be indicated first that the substrate is optionally situated beside the anode, or the substrate may be used as a cathode or an anode. Moreover, the total thickness of all the organic layers is preferably less than 500 nm.

It should be realized that a person having ordinary knowledge in the art may prepare an organic EL element or device based on the disclosure of the conventional technologies and/or the prior arts cited in the specification of the claimed invention and/or the state-of-the-art processes. The suitable materials of the layers of an organic EL device other than the hole-injection layer are described below:

Substrate

The substrate can either be light-transmissive or light tight, depending on the light direction. For applications where the EL emission is viewed from the substrate, transparent glass or organic materials having light transmissibility are commonly employed in these cases. On the other hand, for applications where the EL emission is viewed from the top electrode, the transmissibility of the bottom support becomes immaterial and therefore the support can be light transmissive, light absorbing or light reflective. Substrates for use in this case include, but are not limited to, glass, plastic, semiconductor materials, ceramics and circuit board materials. Nevertheless, it is necessary to provide these devices with a light-transparent top electrode.

Anode

The conductive anode layer is commonly formed on the top of the substrate. Moreover, when EL emission is viewed from the anode, the anode should be transparent or substantially transparent to the some emissions. Common transparent anode materials such as indium tin oxide (IPO) may be used in the claimed invention. Other suitable metal oxides include, but are not limited to, aluminum- or indium-doped zinc oxide (IZO), magnesium-indium oxide and nickel-tungsten oxide. In addition to the said oxides, metal nitrides such as gallium nitride, metal selenides such as zinc selenide and metal sulfides such as zinc sulfide may be used in the said layer. For applications where EL emission is viewed from the top electrode, the transmissive characteristics of the said layer are immaterial and any conductive, transparent, opaque or reflective materials may be used. Suitable materials for this application include, but are not limited to, gold, iridium, molybdenum, palladium and platinum. Typical anode materials, regardless of transparency, have a work function of 4.1 eV or greater. Desired anode materials may be deposited by any suitable means such as evaporation, sputtering, chemical vapor deposition or electrochemical means. Moreover, anodes may be patterned using conventional photolithographic processes.

Hole-Transporting Layer (HTL)

The hole-transporting layer of an organic EL device contains at least one hole-transporting compound such as an aromatic tertiary amine, which is understood to be a compound containing at least one trivalent nitrogen atom that is linked only to a carbon atom, at least one of which is a member of an aromatic ring. The said aromatic tertiary amines may be arylamine, such as a monoarylamine, diarylamine, triarylamine or polymeric arylamine group. Exemplary monomeric triarylamines are illustrated by Klupfel et al. in U.S. Pat. No. 3,180,730. Other suitable triarylamines substituted with one or more vinyl radicals and/or at least one active hydrogen-containing group are disclosed by Brantley et al., U.S. Pat. Nos. 3,567,450 and 3,658,520.

A more preferred class of aromatic tertiary amines are those having at least two aromatic tertiary amine moieties, as described in U.S. Pat. Nos. 4,720,432 and 5,061,569. Such compounds may be represented by the formula (A):

(A)

wherein $Q_1$ and $Q_2$ are independently selected from aromatic tertiary amine groups and G is a linking group such as arylene, cycloalkylene or alkylene. In one embodiment, at least one of $Q_1$ and $Q_2$ contains a polycyclic fused ring group such as naphthalene. When G is an aryl group, it is conveniently a phenylene, biphenylene or naphthalene group.

A useful class of triarylamine groups conforming to the formula (A) and containing two triarylamine groups is represented by the formula (B):

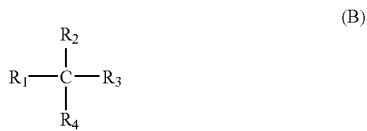

wherein $R_1$ and $R_2$ each independently represent a hydrogen atom, an aryl group or an alkyl group, or $R_1$ and $R_2$ may form a cycloalkyl group; $R_3$ and $R_4$ each independently represent an aryl group, which is in turn substituted with a diaryl substituted amino group, as indicated by the formula (C):

wherein $R_5$ and $R_6$ are independently selected from aryl groups. In one embodiment, at least one of $R_5$ and $R_6$ contains a polycyclic fused ring group such as naphthalene.

Another class of aromatic tertiary amine groups is the tetraaryldiamines. Desirable tetraaryldiamines include two diarylamino groups represented by the formula (C) linked together via an arylene group. Useful tetraaryldiamines include those having the formula (D):

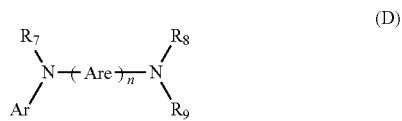

wherein each Are is independently selected from arylene group such as phenylene or anthracene group; n is an integer from 1 to 4; and Ar, $R_7$, $R_8$ and $R_9$ are independently selected from aryl groups. In a typical embodiment, at least one of Ar, $R_7$, $R_8$ and $R_9$ is a polycyclic fused ring group such as naphthalene.

The compound of the aforementioned formula (A), (B), (C) and (D) may be substituted with different alkyl, alkylene, aryl and arylene. Typical substituents comprise alkyl, alkoxy, aryl, aryloxy and halogen such as fluorine, chlorine and bromine, etc. The said alkyl and alkylene groups typically contain 1 to 6 carbon atoms. The said cycloalkyl group may contain 3 to 10 carbon atoms, but typically contain 5, 6 or 7 ring carbon atoms such as cyclopentyl, cyclohexyl and cycloheptyl. The said aryl and arylene groups are usually phenyl and phenylene groups.

The hole-transporting layer may be formed of a single or a mixture of aromatic tertiary amine compounds. For example, a triarylamine such as a triarylamine of the formula (B) may be used in combination with a tetraaryldiamine of the formula (D). When a triarylamine is used in combination with a tetraaryldiamine, it is positioned as a mono-layer interposed between the electron injecting layer and transporting layer. Examples of useful tertiary amines are listed as below:

1,1-Bis(4-di-p-tolylaminophenyl)cyclohexane
1,1-Bis(4-di-p-tolylaminophenyl)-4-phenylcyclohexane
4,4'-Bis(4-diphenylamino)tetraphenyl
Bis(4-dimethylamino-2-methylphenyl)-phenylmethane
N,N,N-Tri(p-tolyl)amine
4-(di-p-tolylamino)-4'-[4(di-p-tolylamino)-styryl]stilbene
N,N,N',N'-tetra-p-tolyl-4,4'-diaminobiphenyl
N,N,N',N'-tetraphenyl-4,4'-diaminobiphenyl
N,N,N',N'-tetra-1-nephthyl-4,4'-diaminobiphenyl
N,N,N',N'-tetra-2-nephthyl-4,4'-diaminobiphenyl
N-Phenylcarbazole
4,4'-Bis[N-(1-naphthyl)-N-phenylamino]biphenyl
4,4'-Bis[N-(1-naphthyl)-N-(2-naphthyl)amino]biphenyl
4,4"-Bis[N-(1-naphthyl)-N-phenylamino]$_p$-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthyl)-N-phenylamino]biphenyl
4,4"-Bis[N-(1-anthyl)-N-phenylamino]$_p$-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis(di-(1-naphthyl)amino)naphthalene
2,6-Bis(N-(1-naphthyl)-N-(2-naphthyl)amino)naphthalene
N,N,N',N'-Tetra(2-naphthyl)-4,4"-diamino-p-terphenyl
4,4'-Bis{N-phenyl-N-[4-(1-naphthyl)-phenyl]amino}biphenyl
4,4'-Bis[N-(2-pyrenyl)amino]biphenyl
2,6-Bis[N,N-di(2-naphthyl)amine]fluorene
1,5-Bis[N-(1-naphthyl)-N-phenylamino]naphthalene Another class of useful hole-transporting materials includes polycyclic aromatic compounds as described in EP 1009041. Moreover, the polymeric hole-transporting materials may also be used. Examples of the polymeric hole-transporting material include poly(N-vinylcarbazole) (PVK), polythiophenes, polypyrrole, polyaniline and copolymers such as poly(3,4-ethylenedioxythiophene)/poly(4-styrenesulfonate) which is also called PEDOT/PSS.

Light-Emitting layer (LEL)

As described in U.S. Pat. Nos. 4,769,292 and 5,935,721, the light-emitting layer (LEL) of the organic EL element comprises a luminescent or fluorescent material where electroluminescence is produced as a result of electro-hole pair recombination. The light-emitting layer can be comprised of a single material, but more commonly consists of a host light-emitting material and a guest light-emitting material or any dopant emitter. The host material in the light-emitting layer may be an electron-transporting material, a hole-transporting material, or other materials or combination of materials capable of sustaining recombination. The dopant is usually chosen from highly fluorescent dyes, but phosphorescent compounds such as transition metal complexes as described in WO 98/55561, WO 00/18851, WO 00/57676 and WO 00/70655 may also be used. Typically, 0.01 to 10% by weight of dopants are doped into the host material.

An important factor for choosing a dye as a dopant is a comparison of the bandgap potential which is defined as the energy difference between the highest occupied molecular orbital and the lowest unoccupied molecular orbital of a molecule. For efficient energy transfer from the host to the dopant, the bandgap of the dopant must be smaller than that of the host material.

The host and emitting materials that are known and have been used include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721 and 6,020,078.

Metal complexes of 8-hydroxyquinoline and similar derivatives (formula E) constitute one class of useful host light-emitting compounds, and are particularly suitable for electroluminescence at wavelengths longer than 500 nm such as green, yellow, orange and red lights.

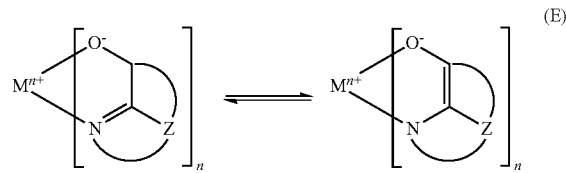

(E)

wherein M represents a metal; n is an integer of 1 to 4; and Z represents an atom in the center of at least two fused aromatic rings.

According to the above descriptions, it should be realized that M may be a monovalent, divalent, trivalent or tetravalent metal. For example, the said metal may be an alkaline metal such as lithium, sodium or potassium, an alkaline earth metal such as magnesium or calcium, an earth metal such as aluminum or gallium, or a transition metal such as zinc or zirconium. Generally, any monovalent, divalent, trivalent or tetravalent metal known as a useful chelatable metal may be employed.

Z represents a heterocyclic nucleus of at least two fused aromatic rings, wherein at least one of the rings is an azole or azine ring. Additional rings, including both aliphatic or aromatic rings, may be fused with the two rings, if desired. To avoid increasing molecular bulk without improving on function, the number of ring atoms is usually maintained at 18 or less.

Examples of useful chelatable oxinoid compounds are listed below

CO-1: tris(8-hydroxyquinolinolato)aluminum(III)

CO-2: bis(8-hydroxyquinolinolato)magnesium(II)

CO-3: Bis[benzo{f}-8-hydroxyquinolinolato]zinc(II)

CO-4: Bis(2-methyl-8-hydroxyquinolinolato)aluminum (III)-μ-oxo-bis(2-methyl-8-hydroxyquinolinolato)aluminum(III)

CO-5: tris(8-hydroxyquinolinolato)indium

CO-6: tris(5-methyl-8-hydroxyquinolinolato)aluminum(III)

CO-7: (8-hydroxyquinolinolato)lithium(I)

CO-8: tris(8-hydroxyquinolinolato)gallium(III)

CO-9: tetra(8-hydroxyquinolinolato)zirconium(IV)

CO-10: Bis(2-methyl-8-hydroxyquinolinolato)-4-phenylphenolatoaluminum(III)

Derivatives of 9,10-di-(2-naphthyl)anthracene (formula F) constitute one class of useful host light-emitter, and are particularly suitable for electroluminescence at wavelengths longer than 400 nm such as blue, green, yellow, orange or red light.

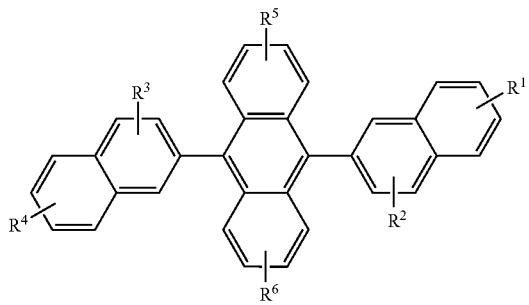

(F)

wherein $R^1$, $R^2$, $R^3$, $R^4$, $R^5$ and $R^6$ represent a hydrogen atom or one or more substituents selected from the following groups:

Group 1: hydrogen, alkyl and alkoxy groups having 1 to 24 carbon atoms;

Group 2: a ring group having 6 to 20 carbon atoms;

Group 3: atoms necessary to form a carbocyclic fused ring group such as naphthyl, anthracenyl, pyrenyl and perylenyl, typically having 6 to 30 carbon atoms;

Group 4: atoms necessary to form a heterocyclic fused ring group such as furyl, thienyl, pyridyl and quinolinyl, typically having 5 to 24 carbon atoms;

Group 5: alkoxyamino, alkylamino and arylamino having 1 to 24 carbon atoms; and

Group 6: fluorine, chlorine, bromine and cyano groups.

Illustrative examples include 9,10-di-(2-naphthyl)anthracene and 2-tert-butyl-9,10-di-(2-naphthyl)anthracene. Other anthracene derivatives that may be used as a host light-emitter in the LEL include derivatives of 9,10-bis[4-(2,2-diphenylethenyl)phenyl)anthracene, and phenylanthracene derivatives described in EP 681019.

Benzazole derivatives (formula G) constitute another class of useful host light-emitter, and are particularly suitable for electroluminescence at wavelengths longer than 400 nm, such as blue, green, yellow, orange or red light.

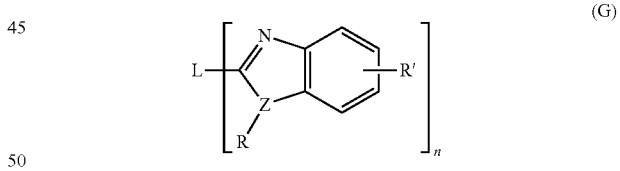

(G)

wherein n is an integer from 3 to 8;

Z is —O, —NR or —S and R is H or a substituent;

R' represents one or more optionally substituents where R and each R' are H or alkyl having 1 to 24 carbon atoms such as propyl, tert-butyl or heptyl group; carbocyclic, heterocyclic ring and fused aromatic ring groups having 5 to 20 carbon atoms such as phenyl, naphthyl, furyl, thienyl, pyridyl and quinolinyl; and halogen such as chlorine and fluoride; and L is a linkage group usually comprising an alkyl or aryl group conjugately or unconjugately attached to multiple benzazoles.

An example of the useful benzazole is 2,2',2"-(1,3,5-phenylene)-tetra[1-phenyl-1H-benzimidazole].

Distyrylarylene derivatives described in U.S. Pat. No. 5,121,029 are also useful host materials in the LEL.

Desirable fluorescent dopants include groups derived from fused ring, heterocyclic and other compounds such as anthracene, tetracene, xanthene, perylene, rubrene, coumarin, rhodamine, quinacridone, dicyanomethylenepyran, thiopyran, polymethine, pyrilium thiapyrilium and carbostyryl compounds. Illustrative examples of useful dopants include, but are not limited to, the following compounds:

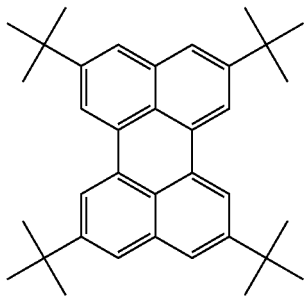

EM1

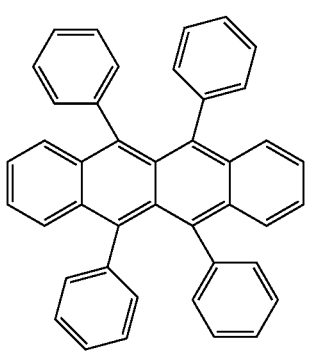

EM2

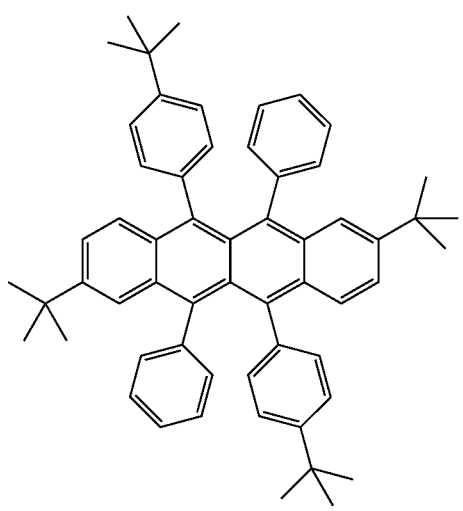

EM3

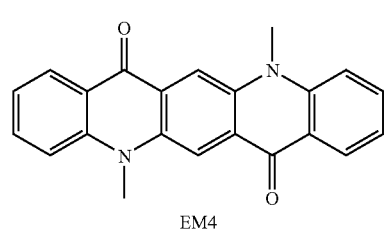

EM4

-continued
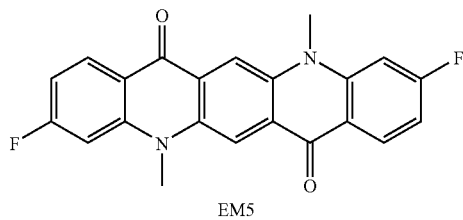
EM5
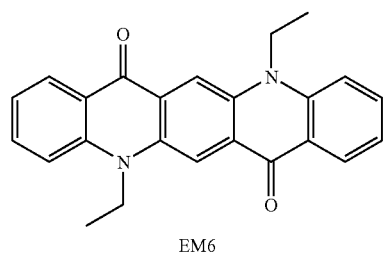
EM6
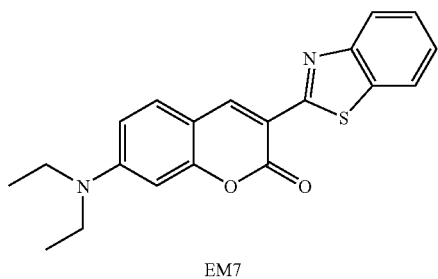
EM7
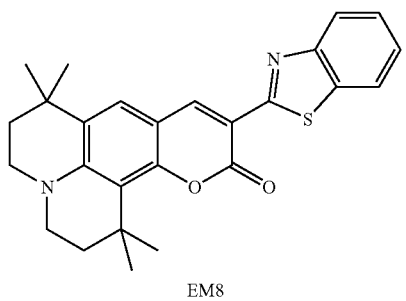
EM8
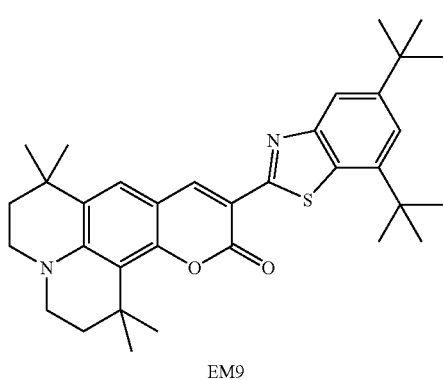
EM9

-continued
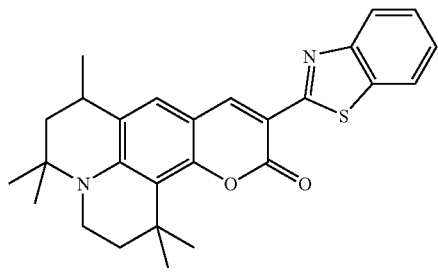
EM10
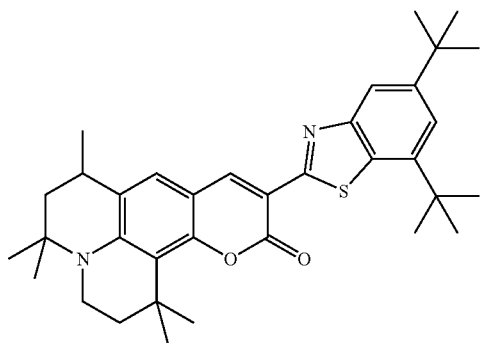
EM11
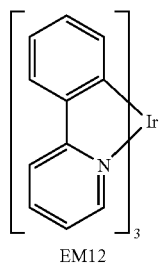
EM12
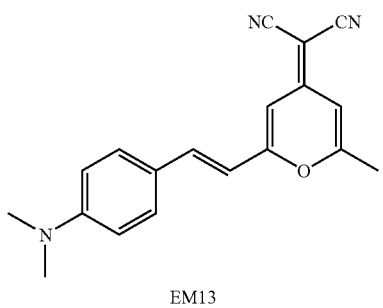
EM13
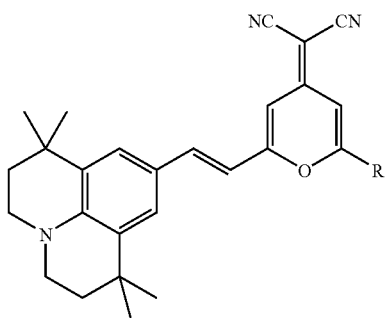
| Compound | R |
|---|---|

-continued
| | |
|---|---|
| EM14 | phenyl |
| EM15 | methyl |
| EM16 | tert-butyl |
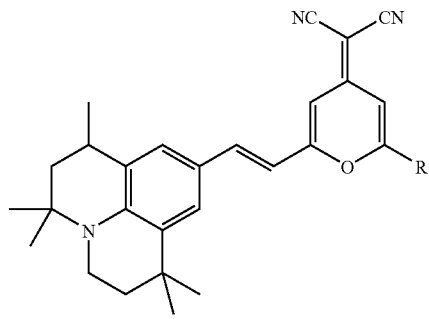
| Compound | R |
|---|---|
| EM17 | phenyl |
| EM18 | methyl |
| EM19 | tert-butyl |
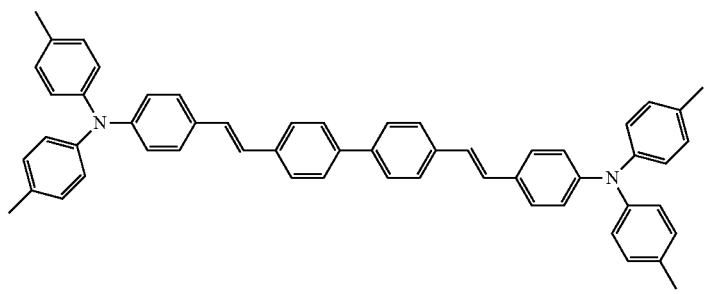
EM20
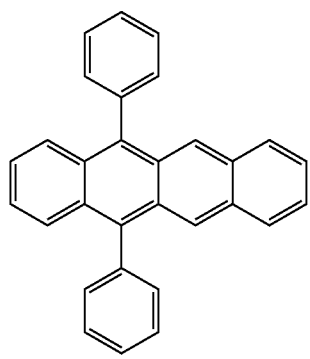
EM21
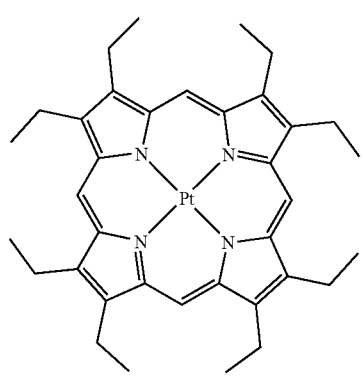
EM22

Electron-Transporting Layer (ETL)

Preferred thin film materials for the electron-transporting layer of the organic EL devices of the claimed invention are metal chelated oxinoid compounds comprising chelates of oxine (commonly referred to as 8-quinolinol or 8-hydroxyquinoline). The said compounds facilitate the injection and transportation of electrons and produce the thin films having high efficiency and easy fabrication. Exemplary of contemplated oxinoid compounds are the compounds having the formula (E) as described above.

Other electron-transporting materials include various butadiene derivatives disclosed in U.S. Pat. No. 4,356,429 and various heterocyclic optical brighteners disclosed in U.S. Pat. No. 4,539,507. Benzazoles having the formula (G) are also useful electron-transporting materials.

In certain embodiments of the present invention, the light-emitting layer and the electron-transporting layer may optionally be combined as a single layer that functions as both light emission and electron transportation.

Cathode

In the case of light emission through the anode, the cathode layer used in the present invention may comprise any conductive material. Desirable qualities for materials are good film-forming properties which ensure good contact with the underlying organic layer, thereby improving injection at low voltage; and good stability. Useful cathode materials often contain a low work function metal (<4.0 eV) or metal alloy. One preferred cathode material comprises Mg:Ag alloy wherein the silver content ranges from 1% to 20% as described in U.S. Pat. No. 4,885,221. Another suitable cathode material is in bilayered form comprising a thick layer of conductive metal covered with a thin layer of metal or metal salt having low work function. Such kind of cathode described in U.S. Pat. No. 5,677,572 comprises a thin layer of LiF and a thicker Al layer. Other useful cathode materials include, but are not limited to, those disclosed in U.S. Pat. Nos. 5,059,861, 5,059,862 and 6,140,763.

In the case of light emission through the cathode, the cathode must be transparent or nearly transparent. In these cases, thin layers of metals, transparent conductive oxides, or a combination of the said materials must be used. Optically transparent cathodes have been described in detail in U.S. Pat. No. 5,776,623. Cathode materials may be deposited by evaporation, sputtering or chemical vapor deposition. If desired, patterning may be achieved by many conventional methods including, but are not limited to, through-mask deposition, integral shadow masking described in U.S. Pat. No. 5,276,380 and EP 0732868, laser ablation and selective chemical vapor deposition.

Furthermore, to improve the color of the light, the luminescence efficiency, the luminescence stability, the lifetime of the element, the preparation processes of the elements, etc. of the organic EL device, references may be made to U.S. Pat. Nos. 4,356,429, 4,539,507, 4,720,432, 4,885,211, 5,151,629, 5,150,006, 5,141,671, 5,073,446, 5,061,569, 5,059,862, 5,059,861, 5,047,687, 4,950,950, 4,769,292, 5,104,740, 5,227,252, 5,256,945, 5,069,975, 5,122,711, 5,366,811, 5,126,214, 5,142,343, 5,389,444, 5,458,977, etc.

In another embodiment of the present invention, the said organic EL device is a display. Generally, the said display may be used in a television, a mobile phone, a computer monitor, various personal or domestic devices, devices and/or electrical appliances used in an office and/or a conveyance, or other devices and/or electric equipments comprising a monitor.

EXAMPLES

The present invention is further illustrated by, but is not limited to, the following examples.

Methods and Instruments

Nuclear Magnetic Resonance (NMR) spectroscopy was performed by VARIAN Unity 300 MHz NMR spectrometer, wherein $CDCl_3$ was used as an internal standard.

Mass spectroscopy was performed by MICROMASS TRIO-2000 GC/MS, wherein the fast atom bombardment (FAB) method was used for the ionization process.

The glass transition temperature (Tg) of an object compound was determined by Perkin Elmer Pryis 1 Differential Scanning Calorimeter (DSC), wherein the flow velocity of the nitrogen gas is 20.0 ml/min. At the beginning, a sample was heated from 50° C. to 400° C. at a heating rate of 20° C./min and then cooled from 400° C. to 50° C. at a cooling rate of 80° C./min. After maintaining at 50° C. for 3 minutes, the said sample was heated again to 200° C. at a heating rate of 10° C./min. The Tg of the target sample was defined as the final transition temperature of the secondary DSC heating curve.

The vacuum thin film evaporation was performed by TRC 18-inches spin coater.

The colorimetry was measured by a PhotoResearch PR-650 colorimeter.

The power was supplied by a programmable power supply of KEITHLEY 2400 instrument.

Preparation of the Elements

The element of the organic EL device may be prepared according to the following procedures:

1. The cleaning of the substrate:

An etched ITO substrate (40×40 mm) was sequentially washed by acetone, methanol and deionized water, then the said ITO substrate was baked in an oven at 130° C. for 1 hour;

2. Pre-treatment of the substrate:

After baking, the said ITO substrate was placed into a plasma chamber and was activated by conventional activation process;

3. Evaporation:

The said pre-treated ITO substrate was put onto the spin carrier of the TRC evaporation instrument. After the vacuum of the chamber of the evaporator reached $10^{-6}$ torr, the evaporation material was heated. During the evaporation, the evaporation rate was monitored by a quartz sensor. The hole-injection layer, NPB, $Alq_3$, LiF and Al were deposited at rates of 2 Å/s, 4 Å/s, 4 Å/s, 0.1 Å/s and 10 Å/s, respectively.

4. Encapsulation:

The encapsulation cover is made of a glass. After UV adhesive was applied onto the said glass cover, the freshly prepared element and the said glass cover were put into a glove box in nitrogen atmosphere. The ITO substrate and the glass cover were sealed by a press of a heavy article, and the polymerization of the adhesive was initiated by UV light.

5. The measurement of the chromaticity and brightness of the element:

Under the control of the LabVIEW software, the encapsulated element was supplied by a power source. The spectrum, brightness and chromaticity ($CIE_{x,y}$) of the said element were measured by a colorimeter.

I. Preparation of the Compounds

Example I-1

The Synthesis of Compound S701

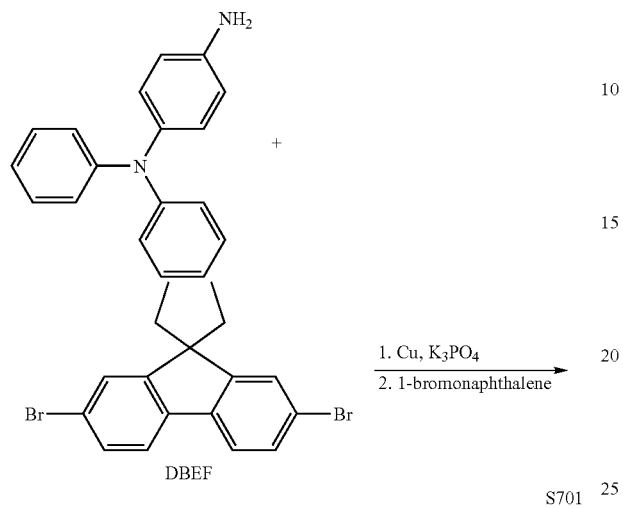

4-amino-triphenylamine (8.9 g), 9,9-diethyl-2,7-dibromofluorene (6.5 g), nitrobenzene (500 mL) and potassium carbonate (14 g) were added into a tri-neck flask. Copper powder (0.6 g) was added under nitrogen, and the reaction mixture was heated at 180° C. for 6 hours with stirring. 1-Bromonaphthalene (7 g) was then added and the reaction continued for another 18 hours. After cooling, the reaction mixture was extracted with water (1.5 L) and ethyl acetate (1.5 L). The solvent was removed under reduced pressure, the residue was purified by the column chromatography and 4.7 g of pale yellow solid was obtained (yield: 28%). MASS-FAB: 992 (M+2)$^+$.

Example I-2

The Synthesis of Compound S702

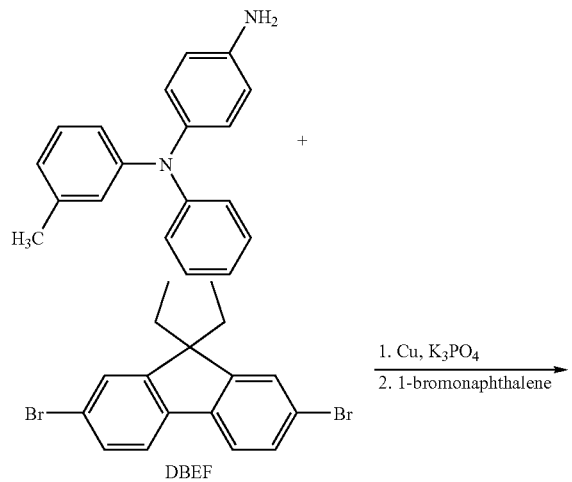

N-(3-methylphenyl)-N-phenyl-1,4-phenylenediamine (8.5 g), 9,9-diethyl-2,7-dibromofluorene (5.8 g), nitrobenzene (500 mL) and potassium carbonate (12.8 g) were added into a tri-neck flask. Copper powder (0.5 g) was added under nitrogen, and the reaction mixture was heated at 180° C. for 6 hours with stirring. 1-Bromonaphthalene (6.5 g) was then added and the reaction continued for another 16 hours. After cooling, the reaction mixture was extracted with water (1.5 L) and ethyl acetate (1.5 L). The solvent was removed under reduced pressure, the residue was purified by the column chromatography and 4.1 g of pale yellow solid was obtained (yield: 26%). MASS-FAB: 1019 (M+1)$^+$.

Example I-3

The Synthesis of Compound S704

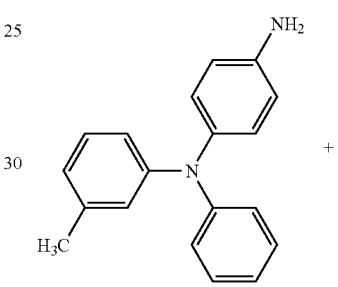

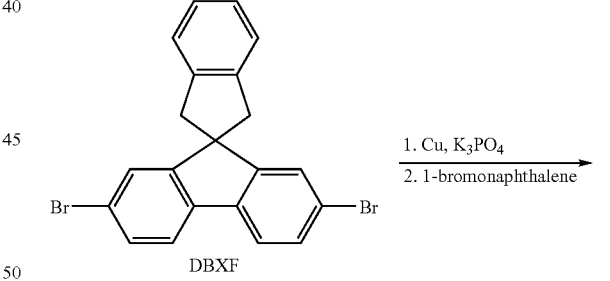

N-(3-methylphenyl)-N-phenyl-1,4-phenylenediamine (10 g), DBXF (7.7 g), nitrobenzene (500 mL) and potassium carbonate (15 g) were added into a tri-neck flask. Copper powder (0.6 g) was added under nitrogen, and the reaction mixture was heated at 180° C. for 6 hours with stirring. 1-Bromonaphthalene (7.6 g) was then added and the reaction continued for another 16 hours. After cooling, the reaction mixture was extracted with water (1.5 L) and ethyl acetate (1.5 L). The solvent was removed under reduced pressure, the residue was purified by the column chromatography and 4.8 g of pale yellow solid was obtained (yield: 25%). MASS-FAB: 1066 (M+2)$^+$.

Example I-4

The Synthesis of Compound S705

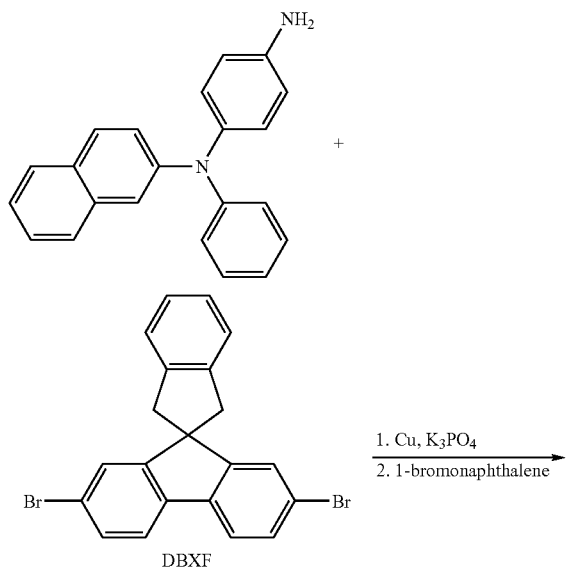

N-(2-naphthyl)-N-phenyl-1,4-phenylenediamine (10 g), DBXF (6.8 g), nitrobenzene (500 mL) and potassium carbonate (13.3 g) were added into a tri-neck flask. Copper powder (0.6 g) was added under nitrogen, and the reaction mixture was heated at 180° C. for 6 hours with stirring. 1-Bromonaphthalene (6.7 g) was then added and the reaction continued for another 16 hours. After cooling, the reaction mixture was extracted with water (1.5 L) and ethyl acetate (1.5 L). The solvent was removed under reduced pressure, the residue was purified by the column chromatography and 4.2 g of pale yellow solid was obtained (yield: 23%). MASS-FAB: 1036 (M+2)$^+$.

Example I-5

The Synthesis of Compound S706

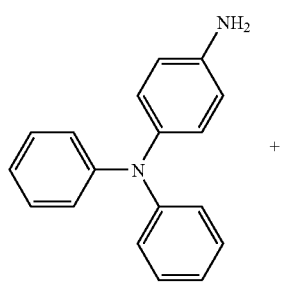

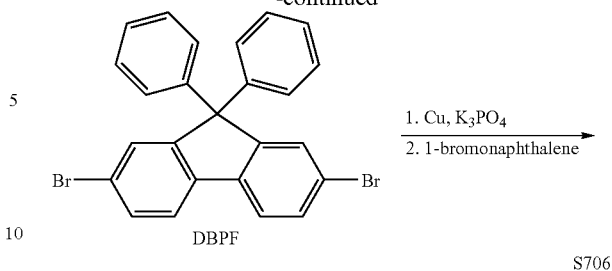

4-Amino-triphenylamine (10.2 g), 9,9-diphenyl-2,7-dibromofluorene (9.4 g), nitrobenzene (500 mL) and potassium carbonate (17 g) were added into a tri-neck flask. Copper powder (0.64 g) was added under nitrogen, and the reaction mixture was heated at 180° C. for 6 hours with stirring. 1-Bromonaphthalene (9.2 g) was then added and the reaction continued for another 18 hours. After cooling, the reaction mixture was extracted with water (1.5 L) and ethyl acetate (1.5 L). The solvent was removed under reduced pressure, the residue was purified by the column chromatography and 6.9 g of pale yellow solid was obtained (yield: 32%). MASS-FAB: 1088 (M+2)$^+$.

Example I-6

The Synthesis of Compound S708

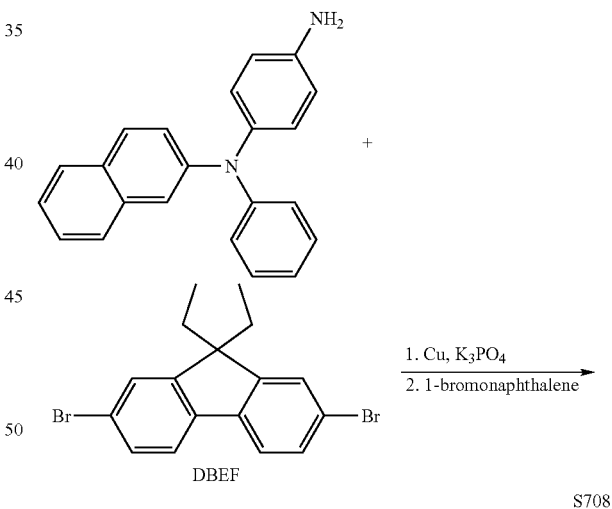

N-(2-naphthyl)-N-phenyl-1,4-phenylenediamine (8.5 g), 2,7-dibromo-9,9-diethyl-fluorene (5.2 g), nitrobenzene (500 mL) and potassium carbonate (9.25 g) were added into a tri-neck flask. Copper powder (0.5 g) was added under nitrogen, and the reaction mixture was heated at 180° C. for 6 hours with stirring. 1-Bromonaphthalene (5.7 g) was then added and the reaction continued for another 16 hours. After cooling, the reaction mixture was extracted with water (1.5 L) and ethyl acetate (1.5 L). The solvent was removed under reduced pressure, the residue was purified by the column chromatography and 4.2 g of pale yellow solid was obtained (yield: 28%). MASS-FAB: 1091 (M+1)$^+$ and 1092 (M+2)$^+$.

II. The Determination of the Glass Transition Temperature (Tg)

Example II-1

Tg of Compounds S701 to S711

According to the previously described method, the Tg of the Compounds S701 to S711 were measured and listed below:

| Compound | Tg (° C.) |
|---|---|
| S701 | 134.2 |
| S702 | 122.9 |
| S703 | 132.4 |
| S704 | 137.6 |
| S705 | 118.8 |
| S706 | 153 |
| S707 | 130.5 |
| S708 | 146.9 |
| S709 | 147.3 |
| S710 | 147.2 |
| S711 | N/A |

Example II-2

Comparative Example, Tg of the Conventional Compounds for the Hole-Injection Layer of an Organic EL Device The conventional compounds for the hole-injection layer of an organic EL device are TPD, NPB, MTDATA and spiro-TPD. The structure formulas of the said compounds are shown below:

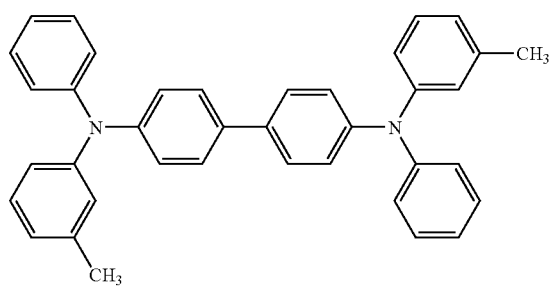

TPD

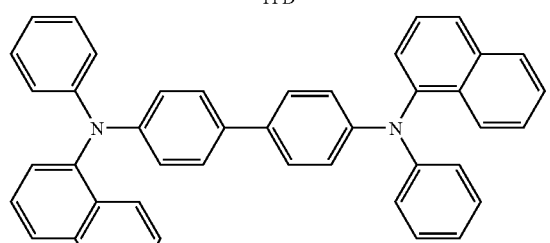

NPB

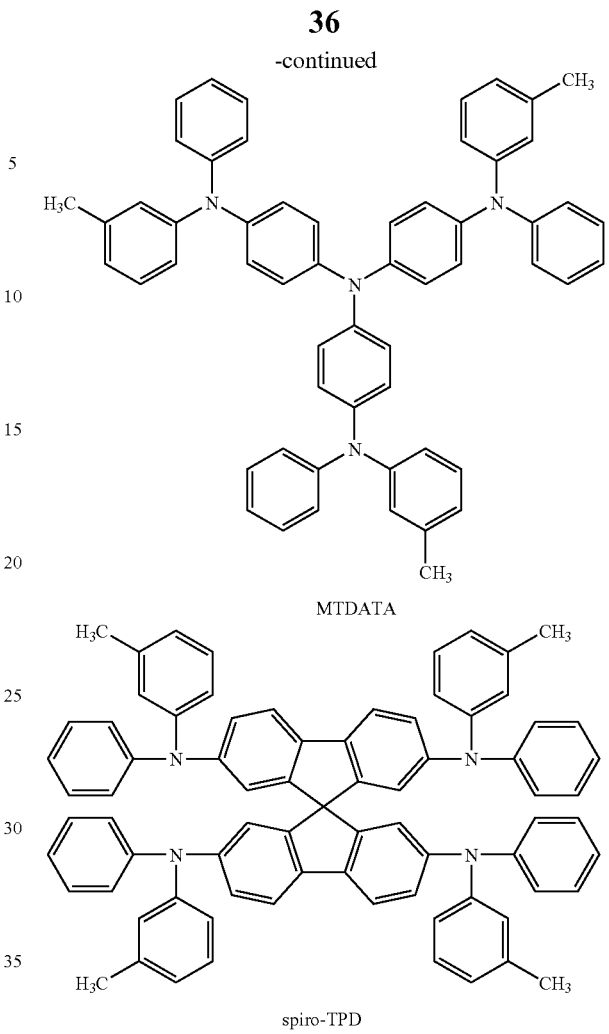

MTDATA spiro-TPD

According to the same method as Example II-1, the Tg of the compounds TPD, NPB, MTDATA and spiro-TPD were measured and listed below:

| Compound | Tg (° C.) |
|---|---|
| TPD | 65 |
| NPB | 98 |
| MTDATA | 75 |
| spiro-TPD | 133 |

III. The Preparation of the Elements Comprising the Compounds of the Claimed Invention and the Measurement of the Color and Brightness of the Said Elements An embodiment of the organic EL device according to the claimed invention may be schematically illustrated in FIG. 1. The organic EL device 10 comprises a transparent glass or plastic substrate 11. A transparent conductive anode 12 was deposited on the surface of the substrate 11 by evaporation and an organic hole-injection material was then deposited on the surface of the anode layer 12 by evaporation to form a hole-injection layer 13. The hole-transporting material is then deposited on the surface of the hole-injection layer by evaporation and thus a hole-transporting layer 14 was formed. The light-emitting layer 15 was then formed on the surface of the layer 14 by the evaporation deposition of the main light-emitting material having fluorescent dopants. An electron-injection material was deposited on the surface of the layer 16 by evaporation to form an electron-injection layer 17. Finally, a metal conductive layer 18 was deposited on the surface of the layer 17 to form a cathode.

In this exemplary embodiment, the conductive anode layer 12 involved a p-type contact and the conductive cathode layer 18 involved a n-type contact. The negative and positive terminals of the electric power source 19 were respectively connected to conductive layers 18 and 12. When a potential was applied between the layers 12 and 18, electrons injecting from the n-type contact (layer 18) passed through the electron-injection layer 17 and the organic electron-transporting layer 16 and then entered the organic light-emitting layer 15. On the other hand, holes injecting from the p-type contact (layer 12) passed through the organic hole-injection layer 13 and the organic hole-transporting layer 14 and then entered the organic light-emitting layer 15. The recombination of said electrons with holes in the organic light-emitting layer 15 resulted in the emission of photons.

According to the methods stated above, the chromaticity and brightness of the elements comprising the Compounds S701 to S711 of the claimed invention were determined and had the results below:

Example III-1

Structure of the element: ITO/S702+2% $F_4$-TCNQ (600 Å)/NPB (200 Å)/Alq$_3$+1% C545T (375 Å)/Alq$_3$ (375 Å)/Li (10 Å)/Al (2000 Å)
Driving potential: 6.64 V
Brightness: 3160 cd/m$^2$
Chromaticity: CIE$_{x,y}$(0.31, 0.64)

Example III-2

Structure of the element: ITO/WO$_3$ (70 Å)/S705 (600 Å)/NPB (200 Å)/Alq$_3$ (700 Å)/Li (10 Å)/Al (2000 Å)
Driving potential: 8.65 V
Brightness: 745 cd/m$^2$
Chromaticity: CIE$_{x,y}$(0.36, 0.55)

Example III-3

Structure of the element: ITO/WO$_3$ (70 Å)/S707 (600 Å)/NPB (200 Å)/Alq$_3$ (700 Å)/Li(10 Å)/Al (2000 Å)
Driving potential: 7.76 V
Brightness: 1002 cd/m$^2$
Chromaticity: CIE$_{x,y}$(0.36, 0.55)

Example III-4

Structure of the element: ITO/S707 (600 Å)/NPB (200 Å)/Alq$_3$ (700 Å)/Li (10 Å)/Al (2000 Å)
Driving potential: 7.19 V
Brightness: 913 cd/m$^2$
Chromaticity: CIE$_{x,y}$(0.36, 0.55)

Example III-5

Structure of the element: ITO/WO$_3$ (70 Å)/S708 (600 Å)/NPB (200 Å)/Alq$_3$ (700 Å)/Li (10 Å)/Al (2000 Å)
Driving potential: 7.11 V
Brightness: 842 cd/m$^2$
Chromaticity: CIE$_{x,y}$(0.35, 0.55)

Example III-6

Structure of the element: ITO/WO$_3$ (70 Å)/S707 (600 Å)/NPB (200 Å)/Alq$_3$+1% C545T (375 Å)/Alq$_3$ (375 Å)/Li (10 Å)/Al (2000 Å)
Driving potential: 7.33 V
Brightness: 3106 cd/m$^2$
Chromaticity: CIE$_{x,y}$(0.31, 0.64)

Example III-7

Structure of the element: ITO/S707 (600 Å)/NPB (200 Å)/Alq$_3$+1% C545T (375 Å)/Alq$_3$ (375 Å)/Li (10 Å)/Al (2000 Å)
Driving potential: 7.17 V
Brightness: 3146 cd/m$^2$
Chromaticity: CIE$_{x,y}$(0.30, 0.64)

Example III-8

Structure of the element: ITO/WO$_3$ (70 Å)/S708 (600 Å)/NPB (200 Å)/Alq$_3$+2% DCJTB (375 Å)/Alq$_3$ (375 Å)/Li (10 Å)/Al (2000 Å)
Driving potential: 9.61 V
Brightness: 345 cd/m$^2$
Chromaticity: CIE$_{x,y}$(0.65, 0.35)

Example III-9

Structure of the element: ITO/S709 (600 Å)/NPB (200 Å)/Alq$_3$+2% DCJTB (375 Å)/Alq$_3$ (375 Å)/Li (10 Å)/Al (2000 Å)
Driving potential: 9.37 V
Brightness: 336 cd/m$^2$
Chromaticity: CIE$_{x,y}$(0.65, 0.35)

Example III-10

Structure of the element: ITO/S709 (600 Å)/NPB (200 Å)/Alq$_3$ (700 Å)/Li (10 Å)/Al (2000 Å)
Driving potential: 11.4 V
Brightness: 476 cd/m$^2$
Chromaticity: CIE$_{x,y}$(0.36, 0.56)

Example III-11

Structure of the element: ITO/S709 (600 Å)/NPB (200 Å)/Alq$_3$+1% C545T (375 Å)/Alq$_3$ (375 Å)/Li (10 Å)/Al (2000 Å)
Driving potential: 12.63 V
Brightness: 2174 cd/m$^2$ (32591 cd/m$^2$ at 19.21 V)
Chromaticity: CIE$_{x,y}$(0.31, 0.64)

Example III-12

Structure of the element: ITO/S709+2% $F_4$-TCNQ (1500 Å)/NPB (200 Å)/Alq$_3$+1% C545T (375 Å)/Alq$_3$ (375 Å)/Li (10 Å)/Al (2000 Å)
Driving potential: 11.69 V
Brightness: 2339 cd/m$^2$ (63693 cd/m$^2$ at 15.15 V)
Chromaticity: CIE$_{x,y}$(0.30, 0.65)

Example III-13

Structure of the element: ITO/S709 (600 Å)/NPB (200 Å)/Alq$_3$+2% DCJTB (375 Å)/Alq$_3$ (375 Å)/Li (10 Å)/Al (2000 Å)
Driving potential: 22.5 V
Brightness: 7914 cd/m$^2$
Chromaticity: CIE$_{x,y}$(0.65, 0.35)

Example III-14

Structure of the element: ITO/S709 (600 Å)/NPB (200 Å)/Alq$_3$+2% rubreneT (375 Å)/Alq$_3$ (375 Å)/Li (10 Å)/Al (2000 Å)
Driving potential: 13.23 V
Brightness: 1907 cd/m$^2$ (30731 cd/m$^2$ at 19.18 V)
Chromaticity: CIE$_{x,y}$(0.49, 0.49)

Example III-15

Structure of the element: ITO/S710 (600 Å)/NPB (200 Å)/Alq$_3$ (700 Å)/Li (10 Å)/Al (2000 Å)
Driving potential: 8.6 V
Brightness: 884 cd/m$^2$
Chromaticity: CIE$_{x,y}$(0.36, 0.53)

The examples of the present invention are for illustrative purpose, but are not intended to limit the claims of the invention. It will be apparent to those skilled in the art that various modifications and variations can be made to the present invention without departing from the scope or spirit of the claimed invention. In view of the forgoing, it is intended that these modification and variation will fall within the scope of the following claims.

What is claimed is:

1. A compound of the formula (I):

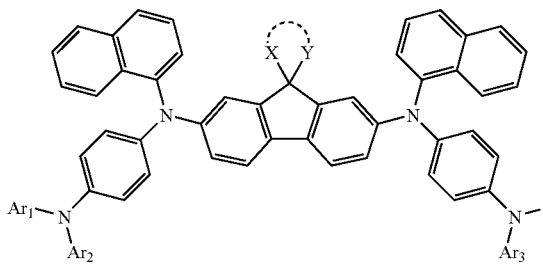

Formula (I)

wherein
X and Y are identical or different, and independently represent straight or branched C$_{1-6}$ alkyl, or C$_{3-8}$ aryl,
Ar$_1$, Ar$_2$, Ar$_3$ and Ar$_4$ are identical or different, and represent optionally substituted C$_{3-8}$ aryl groups.

2. The compound according to claim 1, wherein X and Y are identical or different, and independently represent methyl or ethyl.

3. The compound according to claim 1, wherein X and Y together with C atom to which they are attached may form a benzocyclopentane ring.

4. The compound according to claim 1, wherein X and Y together with C atom to which they are attached may form a fluorene.

5. The compound according to claim 1, wherein Ar$_1$, Ar$_2$, Ar$_3$ and Ar$_4$ are identical or different, and represent optionally substituted phenyl.

6. The compound according to claim 5, wherein Ar$_1$, Ar$_2$, Ar$_3$ and Ar$_4$ are identical or different, and represent phenyl or tolyl.

7. The compound according to claim 1 having the structural formula (II)

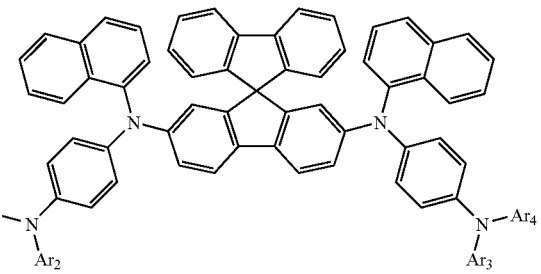

Formula (II)

wherein Ar$_1$, Ar$_2$, Ar$_3$ and Ar$_4$ are identical or different, and represent optionally substituted C$_{3-20}$ aryl groups.

8. The compound according to claim 1 having the structural formula (III)

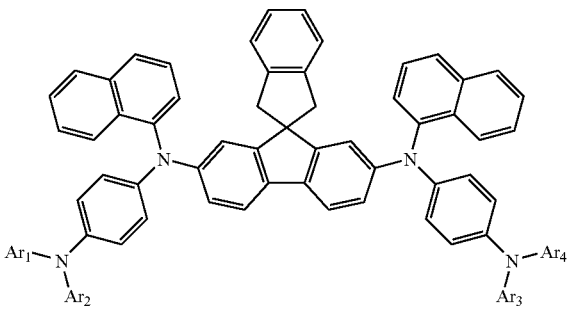

Formula (III)

wherein Ar$_1$, Ar$_2$, Ar$_3$ and Ar$_4$ are identical or different, and represent optionally substituted C$_{3-20}$ aryl groups.

9. The compound according to claim 1 having the structural formula (IV)

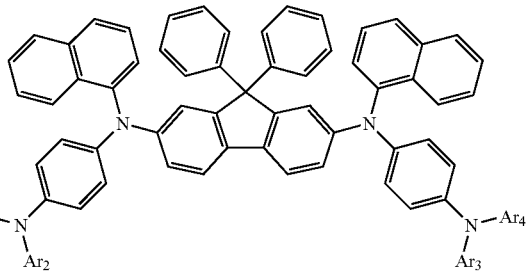

Formula (IV)

wherein Ar$_1$, Ar$_2$, Ar$_3$ and Ar$_4$ are identical or different, and represent optionally substituted C$_{3-20}$ aryl groups.

10. The compound according to claim 1 having the structural formula (V)

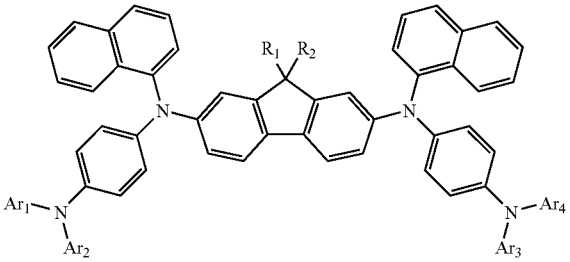

Formula (V)

wherein R$_1$ and R$_2$ are identical or different, and represent C$_{1-6}$alkyl; and Ar$_1$, Ar$_2$, Ar$_3$ and Ar$_4$ are identical or different, and represent optionally substituted C$_{3-20}$ aryl groups.

11. The compound according to any one of claims 7 to 10, which is selected from the following compounds:
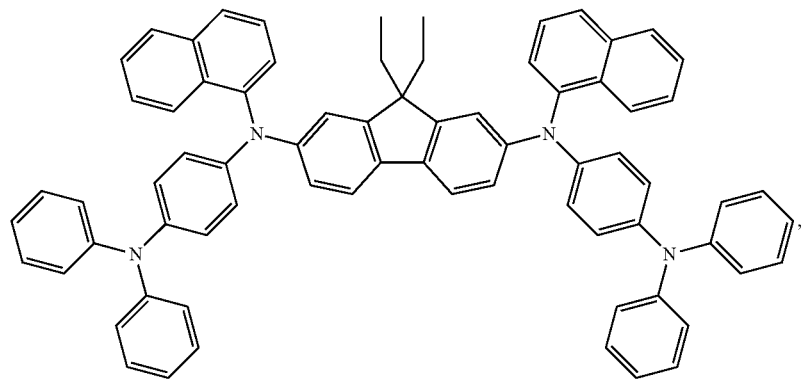
S701
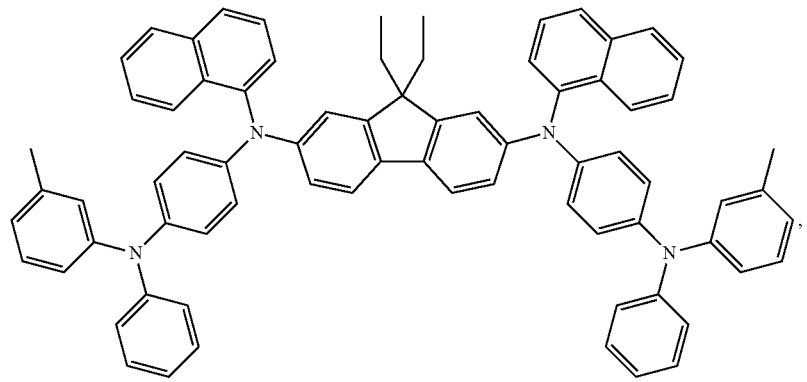
S702
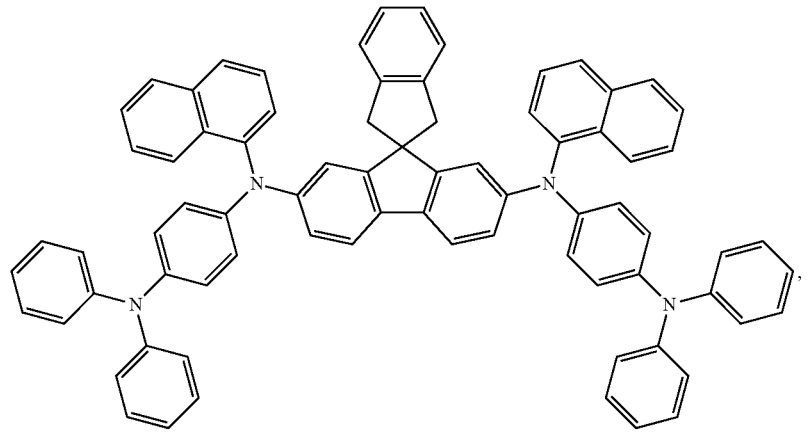
S703
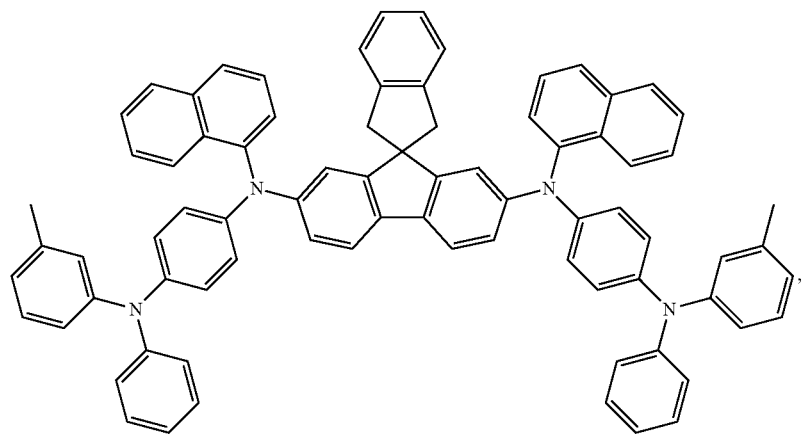
S704

S705
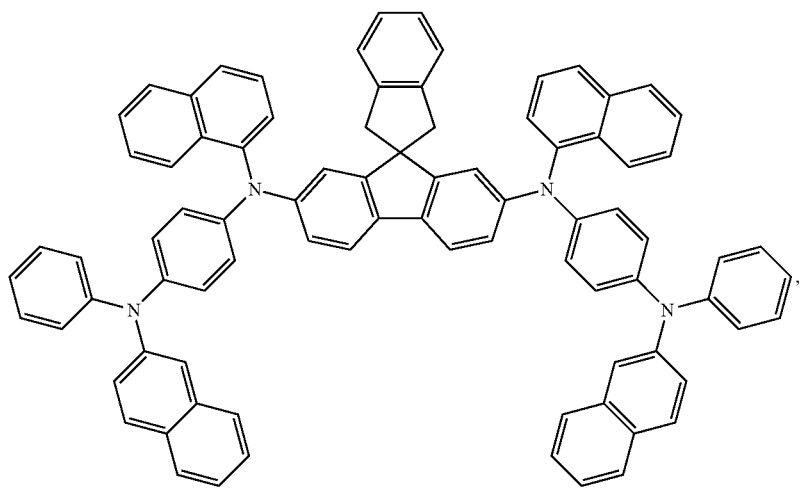
S706
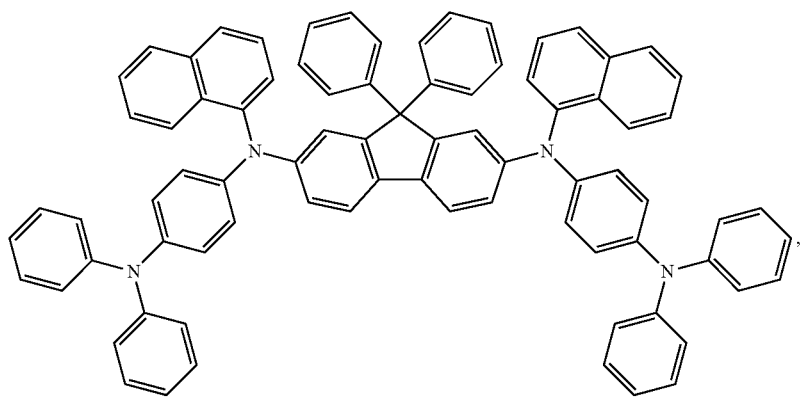
S710
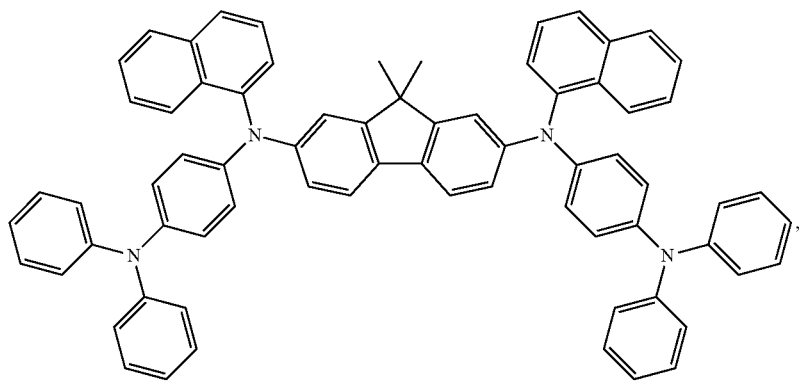
S707
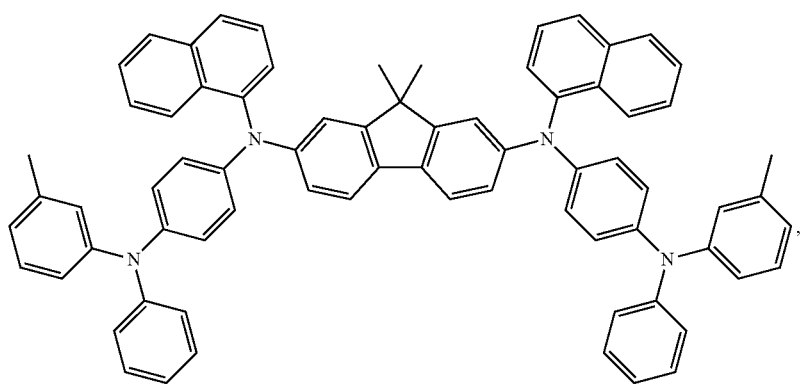

-continued

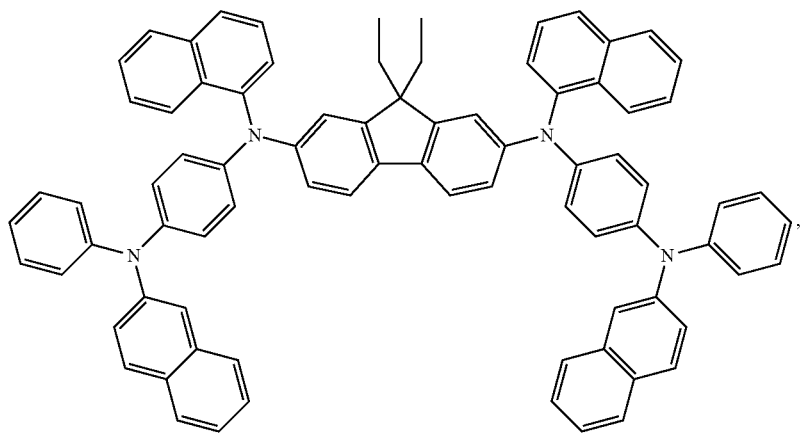
S708

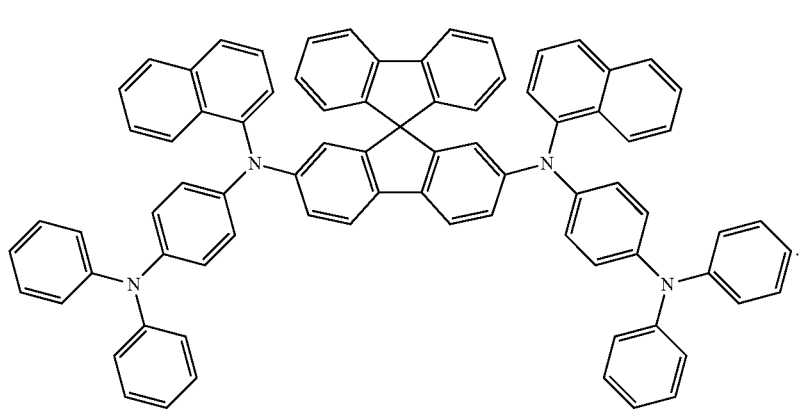
S709

12. The compound according to claim 1, which is used in an organic electroluminescent device.

13. The compound according to claim 12, which is used in the hole-injection layer of an organic electroluminescent device.

14. A process for preparing the compounds according to any one of claims 1 to 13 comprising the following steps:
adding suitable amounts of the compounds having the structural formulas (A) and (B), nitrobenzene and potassium carbonate into a proper container,

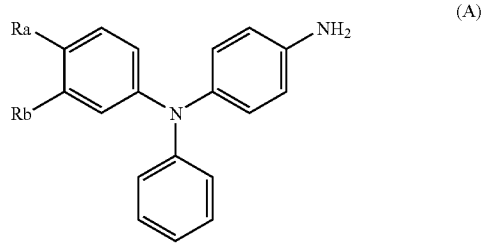
(A)

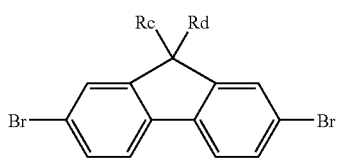
(B)

wherein
Ra and Rb are identical or different, and are independently selected from the group consisting of hydrogen, straight or branched alkyl, alkenyl or alkynyl, cycloalkyl, alkoxy, halo, amino, nitro, cyano, hydroxy, heterocyclyl, aryl and heteroaryl,
or Ra and Rb together with C atom to which they are attached form an optionally substituted saturated or unsaturated cyclohydrocarbon, heterocyclic ring, aryl ring, heteroaryl ring, benzene ring-fused cyclic hydrocarbon, fused benzene ring-fused cyclic hydrocarbon, benzoheterocyclic ring, fused benzene rings-fused heterocyclic ring or polyheterocyclic ring; and
Rc and Rd are identical or different, and are independently selected from the group consisting of hydrogen, straight or branched alkyl, alkenyl or alkynyl, cycloalkyl, alkoxy, halo, amino, nitro, cyano, hydroxy, heterocyclyl, aryl and heteroaryl; or Rc and Rd together with C atom to which they are attached form an optionally substituted saturated or unsaturated cyclohydrocarbon, heterocyclic ring, aryl ring, heteroaryl ring, benzene ring-fused cyclic hydrocarbon, fused benzene ring-fused cyclic hydrocarbon, benzoheterocyclic ring, fused benzene rings-fused heterocyclic ring or polyheterocyclic ring;

adding a suitable amount of copper powder under inert gas;

heating the mixture with stirring; and adding an amount of 1-bromonaphthalene to react.

15. An organic electroluminescent device, which comprises the compound according to any one of claims 1 or 2-13.

16. The organic electroluminescent device according to claim 15, wherein the said organic electroluminescent device is a display.

17. The organic electroluminescent device according to claim 15, wherein the said compound is used as the material for the hole-injection layer.

* * * * *

UNITED STATES PATENT AND TRADEMARK OFFICE
CERTIFICATE OF CORRECTION

PATENT NO. : 7,939,184 B2  
APPLICATION NO. : 11/819576  
DATED : May 10, 2011  
INVENTOR(S) : Shih-Wen Wen et al.

Page 1 of 1

It is certified that error appears in the above-identified patent and that said Letters Patent is hereby corrected as shown below:

Column 18, Line 15:   Replace "4,4"-Bis[N-(1-naphthyl)-N-phenylamino]$_p$-terphenyl" , with -- 4,4"-Bis[N-(1-naphthyl)-N-phenylamino]p-terphenyl --

Column 18, Line 20:   Replace "4,4"-Bis[N-(1-anthyl)-N-phenylamino]$_p$-terphenyl", with -- 4,4"-Bis[N-(1-anthyl)-N-phenylamino]p-terpheyl --

Signed and Sealed this  
Tenth Day of April, 2012

David J. Kappos  
*Director of the United States Patent and Trademark Office*